US010729634B2

(12) United States Patent
Martinez Selva et al.

(10) Patent No.: US 10,729,634 B2
(45) Date of Patent: Aug. 4, 2020

(54) SEX HORMONE-BINDING GLOBULIN FOR USE AS A MEDICAMENT

(71) Applicant: FUNDACIÓ HOSPITAL UNIVERSITARI VALL D'HEBRON—INSTITUT DE RECERCA, Barcelona (ES)

(72) Inventors: David Martinez Selva, Barcelona (ES); Rafael Simó Canonge, Barcelona (ES); Cristina Hernández Pascual, Barcelona (ES); Cristina Saez Lopez, Barcelona (ES); Anna Barbosa Desongles, Barcelona (ES)

(73) Assignee: FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 398 days.

(21) Appl. No.: 14/894,648

(22) PCT Filed: May 29, 2014

(86) PCT No.: PCT/EP2014/061218
§ 371 (c)(1),
(2) Date: Nov. 30, 2015

(87) PCT Pub. No.: WO2014/191542
PCT Pub. Date: Dec. 4, 2014

(65) Prior Publication Data
US 2016/0113852 A1 Apr. 28, 2016

(30) Foreign Application Priority Data

May 30, 2013 (EP) .................................. 13382202

(51) Int. Cl.
*A61K 8/64* (2006.01)
*A61K 38/17* (2006.01)
*A61Q 19/00* (2006.01)
*A61Q 19/06* (2006.01)
*C07K 14/47* (2006.01)

(52) U.S. Cl.
CPC ............ *A61K 8/64* (2013.01); *A61K 38/1722* (2013.01); *A61Q 19/00* (2013.01); *A61Q 19/06* (2013.01); *C07K 14/4717* (2013.01)

(58) Field of Classification Search
None
See application file for complete search history.

(56) References Cited

U.S. PATENT DOCUMENTS

2005/0186290 A1 8/2005 Cals-Grierson
2012/0157378 A1* 6/2012 Liu ..................... C12Q 1/6883
514/6.9

FOREIGN PATENT DOCUMENTS

| EP | 1541127 B1 | 12/2008 |
| WO | WO02/099438 A2 | 12/2002 |
| WO | WO2009033212 A1 | 3/2009 |
| WO | WO2010057135 A2 | 5/2010 |

OTHER PUBLICATIONS

Gershagen, S., et al. 1987 The Journal of Biological Chemistry 262(17): 8430-8437. (Year: 1987).*
Peter, A., et al. 2010 Diabetes 59: 3167-3173. (Year: 2010).*
WebMD reference pages For Cardiovascular Diseases: 5 pages. (retrieved from the internet Nov. 21, 2019) (Year: 2019).*
Sutton-Tyrrell et al., "Sex-hormone-binding Globulin and the Free Androgen Index are Related to Cardiovascular Risk Factors in Multiethnic Premenopausal and Perimenopausal Women Enrolled in the Study of Women Across the Nation (SWAN)", Circulation—2005, Mar. 15, 2005, pp. 1242-1249, vol. 111, Issue 10, Journal of the American Heart Association, Dallas, Texas.
Kalme et al., "Sex Hormone-Binding Globulin and Insulin-like Growth Factor-Binding Protein-1 as Indicators of Metabolic Syndrome, Cardiovascular Risk, and Mortality in Elderly Men", Journal of Clinical Endocrinology & Metabolism, Mar. 2005, first published online Dec. 21, 2004, pp. 1550-1556, vol. No. 90, Issue 3, The Endocrine Society, Washington, D.C.
Stefan et al. "Sex HormoneBinding Globulin and Risk of Type 2 Diabetes." New England Journal of Medicine, Dec. 31, 2009, pp. 2675-2678, vol. 361, No. 27, Massachusetts Medical Society, Boston, MA.
Selva et al, "Monosaccharide-induced lipogenesis regulates the human hepatic sex hormone-binding globulin gene", The Journal of Clinical Investigation, Dec. 3, 2007, pp. 3979-3987, vol. No. 117, Issue 12, The American Society for Clinical Investigation (ASCI), Ann Arbor, Michigan, USA.
Selva et al., "Peroxisome-Proliferator Receptor γ Represses Hepatic Sex Hormone Binding Globulin Expression", Endocrinology, May 2009, first published on line Jan. 29, 2009, pp. 2183-2189, vol. 150, No. 5, Endocrine Society, Washington, DC.
Fortunati et al., "Sex Hormone-Binding Globulin (SHBG), estradiol and breast cancer", Molecular and Cellular Endocrinology, Mar. 5, 2010, pp. 86-92, vol. 316, No. 1, Elsevier Ireland Ltd., Shannon, Co., Clare, Ireland.
Ding, et al., "Sex Hormone-Binding Globulin and Risk of Type 2 Diabetes in Women and Men", New England Journal of Medicine, Sep. 17, 2009, pp. 1152-1163, vol. 361, No. 12, pp. 1152-1163, Massachusetts Medical Society, Boston, MA.

(Continued)

Primary Examiner — Marsha Tsay
(74) Attorney, Agent, or Firm — Peter B. Scull; HDC IP Law LLP

(57) ABSTRACT

Sex hormone-binding globulin and/or any fragment thereof for use as a medicament, in particular for use in the treatment of obesity and hepatic steatosis. The invention also relates to the cosmetic use of the sex hormone-binding globulin and/or any fragment thereof for improving the bodily appearance of a mammal with subcutaneous fat herniated or accumulated within the fibrous connective tissue under the skin, in particular the cosmetic use is for cellulite.

4 Claims, 21 Drawing Sheets
Specification includes a Sequence Listing.

(56) References Cited

OTHER PUBLICATIONS

Perry, et al., "Genetic evidence that raised sex hormone binding globulin (SHBG) levels reduce risk of type 2 diabetes", Human Molecular Genetics, Feb. 1, 2010, pp. 535-544, vol. 19, No. 3, Oxford University Press, Oxford, UK.

Sáez, Cristina "Predoc. Presentation: Desarrollo de un Nuevo modelo de ratón que expresa la SHBG humana", Jan. 2, 2013, p. 1, Retrieved from the Internet: URQ-RAL:http://www.youtube.com/watch?v=q-RAP2FCj4o&feature=player_embedded[retrieved on Aug. 26, 2013] & Cristina Saez: "Vall d'Hebron Institut de Recerca (VHIR) + FollowDesarrollo de un nuevo modelo de raton que expresa la SHBG humana: implicaciones en la obesidad, distribucion de la grasa corporal y diabetes del tipo 2", Vall d'Hebron Institut de Recerca (VHIR), Jan. 2, 2013.

Bocchinfuso et al., "Expression and Differential Glycosylation of Human Sex Hormone-Binding Globulin by Mammalian Cell Lines." Molecular Endocrinology, received Jun. 27, 1991, Accepted Aug. 22, 1991 and first published online Jul. 2, 2013, pp. 1723-1729, vol. 5, Issue 11, Endocrine Society, Washington, DC.

Janne et al., "Human Sex Hormone-Binding Globulin Gene Expression in Trangsgenic Mice", Molecular Endocrinology, Jan. 1, 1997, pp. 123-136, vol. 12, Issue 1, Endocrine Society, Washington, DC.

Pugeat et al., "Sex Hormone-Binding Globulin Gene Expression in the Liver: Drugs and the Metabolic Syndrome", Molecular and Cellular Endocrinology, Mar. 5, 2010, pp. 53-59, vol. 316, No. 1, Elsevier Ireland, Ltd, Clare, Ireland.

International Search Report (ISR), International Application No. PCT/EP2014/061218, International Filing Date May 29, 2014, dated ISR Jan. 8, 2014, 6 pages, European Patent Office, Rijswijk Netherlands.

Extended European Search Report (EESR), European Application No. EP13382202, dated Sep. 11, 2013, 11 pages, European Patent Office, Munich, DE.

Apparent English Translation of the Presentation and Slides: Cristina Sáez, "Predoc. Presentation: Desarrollo de un Nuevo modelo de ratón que expresa la SHBG humana", Jan. 2, 2013, p. 1, Retrieved from the Internet: URQ-RAL:http://www.youtube.com/watch?v=q-RAP2FCj4o&feature=player_embedded[retrieved on Aug. 26, 2013].

Filella, Xavier et al., Prostate Cancer Detection and Prognosis: From Prostate Specific Antigen (PSA) to Exosomal Biomarkers, International Journal of Molecular Sciences, Oct. 26, 2016, pp. 22, vol. 17, Issue 11, MDPI, Basel, Switzerland.

Santos, A-C et al., Central obesity as a major determinant of increased high-sensitivity C-reactive protein in metabolic syndrome, Journal of Obesity, 2005, pp. 1453-1456, vol. 29, Springer Nature, United Kingdom.

Zimmerman, Y. et al., The effect of combined oral contraception on testosterone levels in healthy women: a systematic review and meta-analysis, Human Reproduction Update, 2014, pp. 76-105, vol. 20, No. 1, Oxford University Press on behalf of the European Society of Human Reproduction and Embryology, Oxford, UK.

Harsha Indrasena, Buddhike Sri, Use of thyroglobulin as a tumour marker, World Journal of Biological Chemistry, Feb. 26, 2017, pp. 81-85, vol. 8, Issue 1, Baishideng Publishing Group Inc., Pleasanton, CA.

Saéz-López, Cristina et al., SHBG-057BL/ksJ-db/db: A New Mouse Model to Study SHBG Expression and Regulation During Obesity Development, Dec. 1, 2015, pp. 4571-4581, vol. 156, Issue 12, Endocrinology, Endocrine Society, Washington, D.C.

Syed Ikmal, Sharifah Intan Qhadijah, Potential Biomarkers of Insulin Resistance and Atherosclerosis in Type 2 Diabetes Mellitus Patients with Coronary Artery Disease, International Journal of Endocrinology, 2013, pp. 11, vol. 2013, Hindawi Publishing Corporation, London, UK.

\* cited by examiner (A)

(B)

(A)

(B)

(A)

(B)

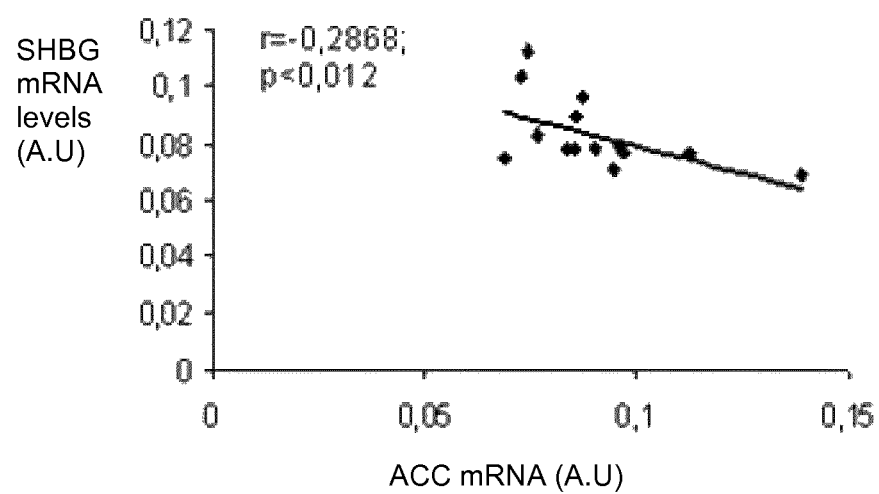
Cont. FIG. 17

(A)

(B)

(C)

(D)
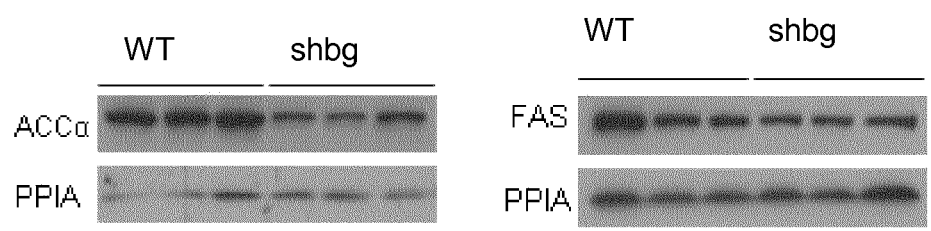
Cont. FIG. 18

(a)

(b)

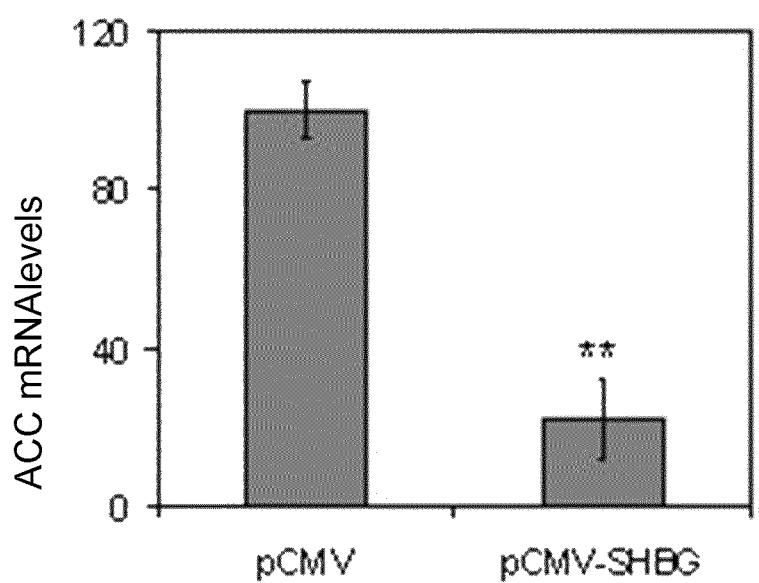
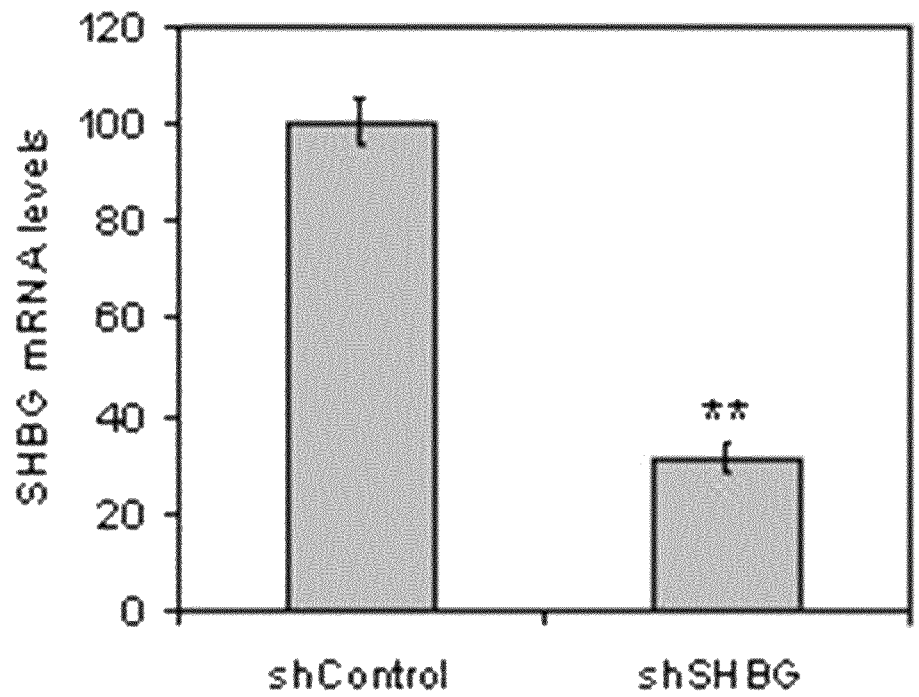
Cont. FIG. 20

(e)
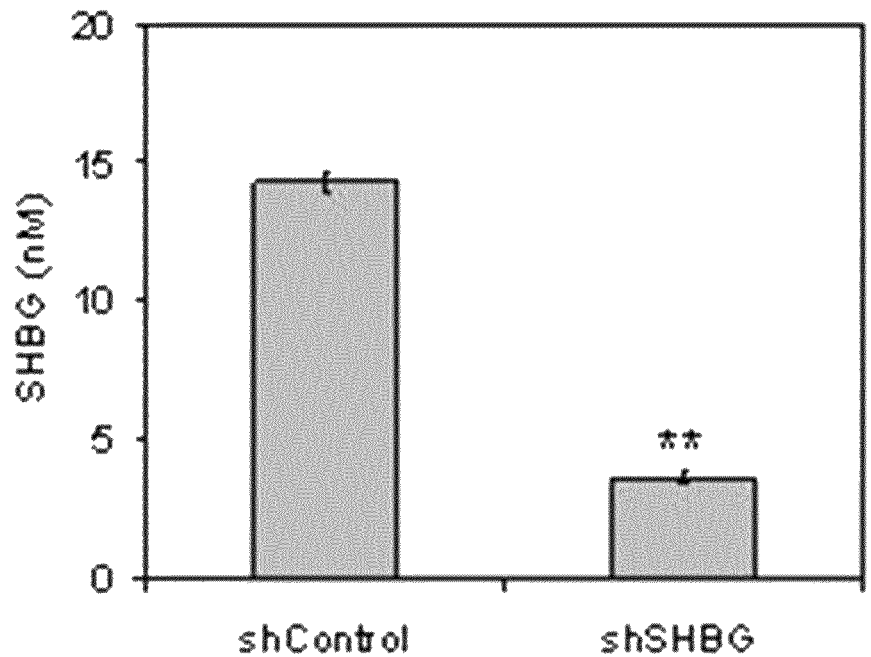
(f)
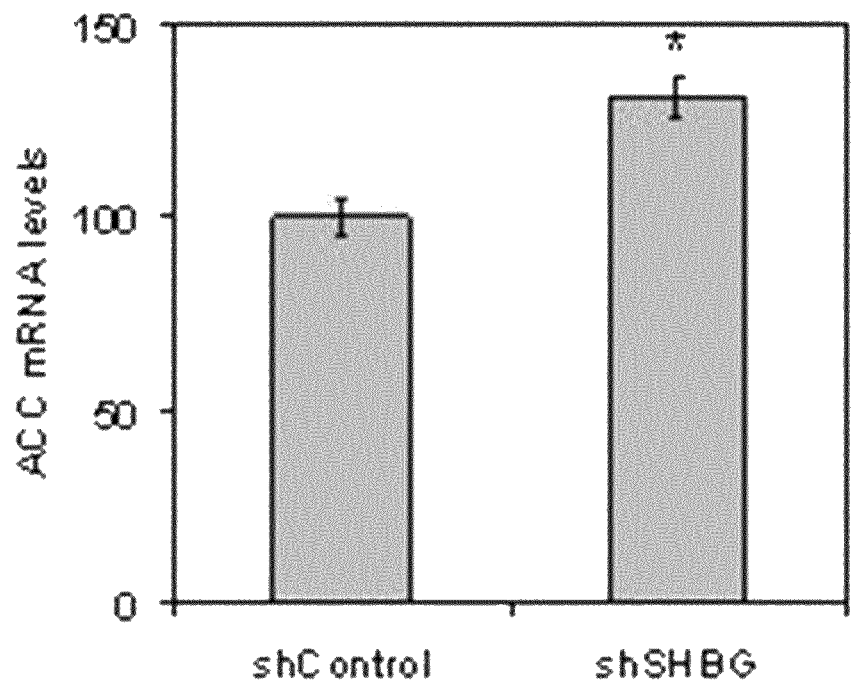
Cont. FIG. 20

(g)
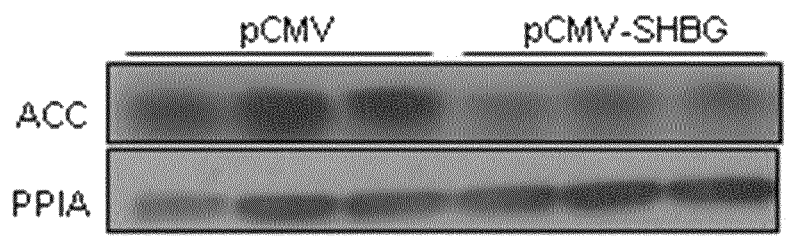
(h)
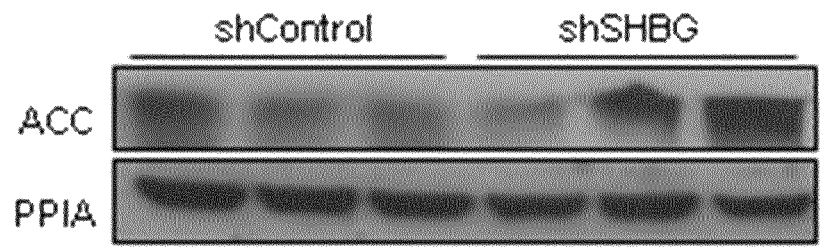
(i)
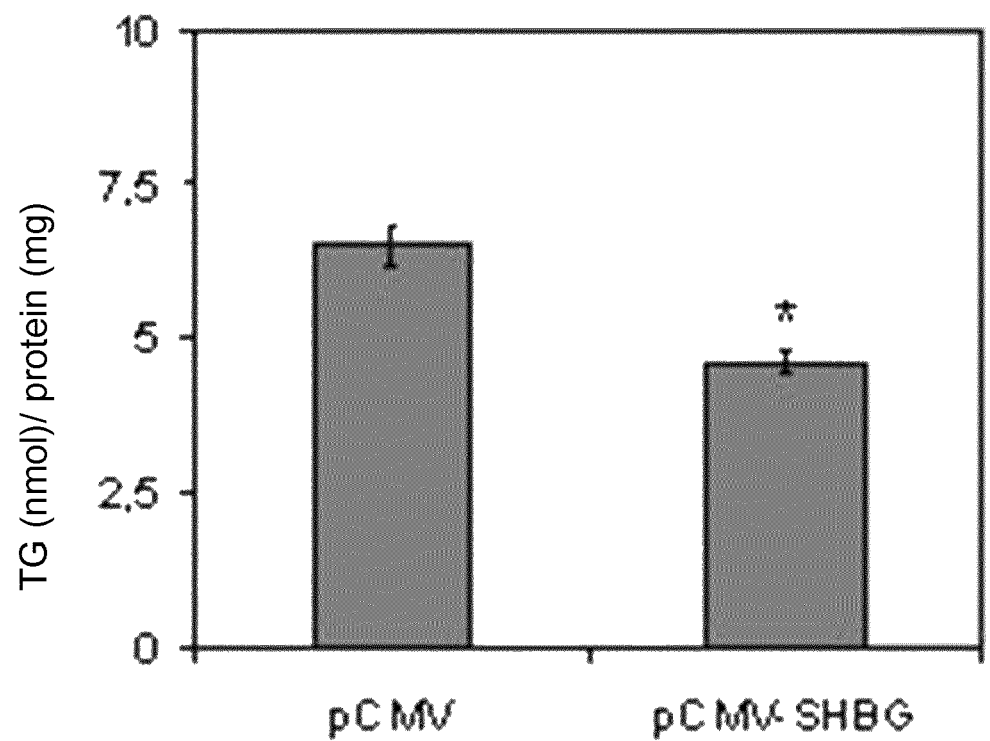
Cont. FIG. 20

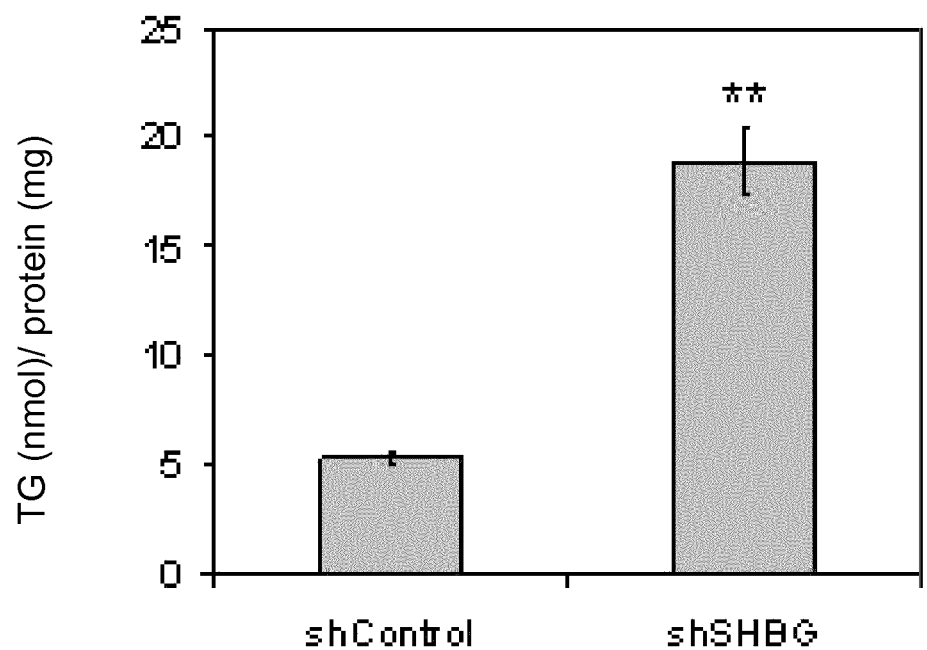
Cont. FIG. 20

SEX HORMONE-BINDING GLOBULIN FOR USE AS A MEDICAMENT

The present invention relates to the field of medical approaches for diseases in which lipid accumulation takes place in one or several animal tissues and organs, such as overweight, obesity, hepatic steatosis or some cardiovascular diseases. The invention also applies to cosmetic methods for reducing lipid stores or body weight.

BACKGROUND ART

Obesity (or adipocity) is a multifactorial metabolic disorder caused from an imbalance between energy intake and expenditure that may have genetic and/or behavioral factors affecting the quantity and quality of food intake as well as lifestyle. It is characterized by increased body weight accompanied by an important deregulation of the adipose tissue function. Obesity is associated with a cluster of chronic and progressive diseases including type 2 diabetes, hyperinsulinemia, dyslipidemia, hepatic pathologies and inflammation among others. On the other hand, overweight is generally defined as having more body fat than is optimally healthy. Being overweight is a common condition, especially where food supplies are plentiful and lifestyles are sedentary.

In biology, adipose tissue or body fat or just fat is loose connective tissue composed mostly of adipocytes. In addition to adipocytes, adipose tissue contains the stromal vascular fraction (SVF) of cells including preadipocytes, fibroblasts, vascular endothelial cells and variety of immune cells (i.e. adipose tissue macrophages (ATMs)). Adipose tissue is derived from preadipocytes. Its main role is to store energy in the form of lipids, although it also cushions and insulates the body. Adipose tissue has in recent years been recognized as a major endocrine organ that produces hormones such as leptin, estrogen, resistin, and the cytokineTNFα. Adipose tissue can affect other organ systems of the body and may lead to disease. Obesity or being overweight in humans and most animals depends on the amount of body fat (adipose tissue). There are two types of adipose tissue, the white adipose tissue (WAT) and brown adipose tissue (BAT).

The main treatment for obesity consists mainly in the worlwide known slimming dieting and physical exercise. Diet programs may produce weight loss over the short term, but maintaining this weight loss is frequently difficult and often requires making exercise and a lower food energy diet a permanent part of a person's lifestyle. Among the known active principles indicated for the treatment of obesity orlistat (Xenical), is current widely available and approved for long term use. Weight loss however is modest with an average of 2.9 kg (6.4 lb) at 1 to 4 years and there is little information on how these drugs affect longer-term complications of obesity. In addition orlistat is associated with gastrointestinal side effects and concerns have been raised about negative effects on the kidneys. Two other medications are also available. Lorcaserin results in an average 3.1 kg weight loss (3% of body mass) greater than placebo over a year. A combination of phentermine and topiramate (Qsymia) is also somewhat effective. On the other hand, obesity is also faced by means of bariatric surgery (reducing the size of the stomach or by resecting and re-routing the small intestines to a small stomach pouch). Surgery for severe obesity is associated with long-term weight loss and decreased overall mortality. However, due to its cost and the risk of complications, researchers are searching for other effective yet less invasive treatments.

Reduction of body adipose tissue is also a cosmetic issue. For instance, there exist many cosmetical compositions with the aim of reducing fat stores in specific areas of the body (thigh, hips, and abdomen). As an example, the patent document EP1541127B1 discloses the use of modulators of aquaglyceroporin adipose (AQPap) in cosmetic compositions as slimming agents. The modulators are selected from coca powder extracts, sapogenins and lycopene in nanocapsules that stimulate AQPap activity, and compounds that enhances AQPap synthesis, such as aescin, complexes of phospholipids and retinoids. The composition may also comprise lypolitic slimming agents and/or lipogenesis inhibitor and/or adipocyte differentiation inhibitor. The lipolytic agent may be a phosphodiesterase inhibitor, a inhibitor of LDL or VLDL receptors, lipolytic peptides and lipolytic proteins.

Hepatic steatosis, also known as Fatty liver, or fatty liver disease (FLD), is a condition where large vacuoles of triglyceride fat accumulate in liver cells via the process of steatosis (i.e. abnormal retention of lipids within a cell). Despite having multiple causes, fatty liver can be considered a single disease that occurs worldwide in those with excessive alcohol intake and those who are obese (with or without effects of insulin resistance). Among these causes, hepatic steatosis is associated with alcohol or metabolic syndrome (diabetes, hypertension, obesity and dyslipidemia), but can also be due to any one of many causes. As for the diagnosis, most individuals are asymptomatic and are usually discovered incidentally because of abnormal liver function tests or hepatomegaly noted in unrelated medical conditions. Elevated liver enzymes are found in 50% of patients with simple steatosis. The serum alanine transaminase level usually is greater than the aspartate transaminase level in the nonalcoholic variant and the opposite in alcoholic FLD (AST:ALT more than 2:1). Currently, the treatment of fatty liver depends on its cause, and generally, treating the underlying cause will reverse the process of steatosis if implemented at an early stage.

Therefore, due to high prevalence of some of the above-mentioned diseases, and of the non-resolutive at all therapeutically approaches for them, it is noteworthy the need of much additional treatment approaches to face all those diseases in which an abnormal accumulation of fat is present in some animal tissues.

SUMMARY OF THE INVENTION

The inventors have found that the protein sex hormone-binding globulin reduced the lipid content in mammal cells, namely due to its role as lipolytic agent, as well as inhibitor of the lipogenesis route.

Thus, in one aspect the invention relates to the sex hormone-binding globulin and/or any fragment thereof for use as a medicament.

Another aspect of the invention is the sex hormone-binding globulin and/or any fragment thereof for use to reduce lipid content in cells of a mammal.

This aspect of the invention can also be formulated as the use of sex hormone-binding globulin as defined above for the manufacture of a medicament for reducing lipid content in cells of a mammal. The present invention also relates to a method for reducing lipid content in cells of a mammal in need thereof, including a human, the method comprising administering a therapeutically effective amount of the sex hormone-binding globulin, together with pharmaceutically acceptable excipients and/or carriers.

The Sex hormone-binding globulin (SHBG) or sex steroid-binding globulin (SSBG) is a dimeric plasma glycoprotein with a molecular mass of about 90 kDa (two subunits). This glycoprotein binds to sex hormones, to be specific, androgens and estrogens. Other steroid hormones such as progesterone, cortisol, and other corticosteroids are bound by transcortin. In human SHBG is produced mostly by the liver and is released into the bloodstream. Other sites that produce SHBG include the brain, uterus, testes, and placenta. Testes-produced SHBG is called androgen-binding protein. The gene for SHBG is located on chromosome 17.

In humans, SHBG is expressed as 5 different isoforms due to alternative splicing. A protein isoform is an alternative forms or expression of the same protein in an organism, derived from different genes or from a unique gene by alternative splicing. The Accession number of these five human isoforms correspond to the UniProtKB/Swiss-Prot database numbers (accessible from NCBI): UniProt P04278-1 for isoform 1 (SEQ ID NO: 1); UniProt P04278-2 for isoform 2 (SEQ ID NO: 2); UniProt P04278-3 for isoform 3 (SEQ ID NO: 3); UniProt P04278-4 for isoform 4 (SEQ ID NO: 4); and UniProt P04278-5 for isoform 5 (SEQ ID NO: 5), all from Apr. 1, 1990, Version 2. The canonical sequence is that of Isoform 1 containing 402 amino acids. All positional information from the others isoforms refer to it. Isoform 1 and isoform 2 are mostly present in liver and testis. The protein can contain post-translation modifications, such as lapidated residues and glycosilations (O-Glycosilation and N-Glycosilations). The nucleotide transcript from which alternative splicing takes place correspond to several sequences identified in the NCBI database with the Accession Number NM_001040, from 12 May 2013, Version 3; or X05403, from 21 Mar. 1995, Version 1.

SHBG is present in all mammals. In mice, the protein has 403 amino acids (SEQ ID NO: 6) and there is only one isoform that is further modified (glycosylation, disulfide bonds) after translation. The Accession Number from the UniProtKB/Swiss-Prot database is P97497 from May 1, 1997, Version 1. The corresponding nucleotide transcript from which the protein derives is the entry of NCBI database with the Accession Number NM_011367, 18 Apr. 2013, Version 2.

As above exposed, in humans the protein sex hormone-binding globulin (SHBG) is expressed in the liver. The expression is under control of hormones and nutritional factors. The human liver secretes SHBG to the blood where it binds androgens and estrogens with high affinity regulating their bioavailability. Body mass index is a major determinant of SHBG concentrations in the blood of men and women. Low serum SHBG levels in overweight individuals are a biomarker for the metabolic syndrome and are predictive of type 2 diabetes and cardiovascular disease risk. Examples of the use of SHBG as biomarker can be found in the document of Sutton-Tyrrell et al., "Sex-hormone-binding Globulin and the free androgen index are related to cardiovascular risk factors in multiethnic premenopausal and perimenopausal women enrolled in the Study of Women Across the Nation (SWAN)", *Circulation*—2005, Vol. No. 111, pp: 1242-1249. Other document indicating SHBG as biomarker is that of Kalme et al., "Sex hormone-binding globulin and insulin-like growth factor-binding protein-1 as indicators of metabolic syndrome, cardiovascular risk, and mortality in elderly men", *J. Clin. Endocrinol. Metab*—2004, Vol. No. 90, pp: 1550-1556. In addition, SHBG measurements are used in clinical bases to determine the amounts of free estradiol and testosterone and to detect metabolic disorders and other diseases.

Another document indicating SHBG as marker for the risk of a disease is the one of Stefan et al. "Sex-Hormone-Binding Globulin and Risk of Type 2 Diabetes", *The New England Journal of Medicine*—2009, 361, pp. 2675-2678. In this document it is also depicted the relationship between the levels of SHBG and Liver Fat in humans. Although it is postulated that the conditions inducing fatty liver may be logical targets when aiming to increase levels of sex hormone-binding globulin in humans, no data are provided.

Not much is known about the mechanistic routes implied in the processes involving SHBG. Nonetheless, there are real evidences that expression of SHBG in hepatocytes could be suppressed by either fructose or glucose. This data are derivable from Selva et al, "Monosaccharide-induced lipogenesis regulates the human hepatic sex hormone-binding globulin gene", *The Journal of Clinical Investigation*—2007, Vol. NO. 117 (12), pp: 3979-3987. In this document Selva et al. showed that the suppression of SHBG levels was due to the reduced hepatic levels of hepatocyte nuclear factor-4α (HNF-4α) due to monosaccharide-induced lipogenesis.

In any of the above disclosed documents the SHBG has never been proved to be effective as therapeutically agent or as prophylactic agent. Thus, the present invention represents the first time these effects of SHBG is disclosed, and due to the extent of the therapeutically effect, and of the conclusive data, it has to be considered a real contribution to the art.

Another aspect of the invention is the use of a cosmetically effective amount of SHBG and/or any fragment thereof, for improving the bodily appearance of a mammal with subcutaneous fat herniated or accumulated within the fibrous connective tissue under the skin.

This aspect of the invention encompasses the cosmetic application of those effective amounts of SHBG in mammals, including human (men and women), which are healthy mammals and that have fat accumulation in the subcutaneous area. In these mammals SHBG can be applied with only esthetical purposes for improving the bodily appearance with dosages usually lower than the therapeutically effective amounts employed when SHBG is used as a medicament.

Yet another aspect of the invention is the use of SHBG and/or any fragment thereof as lipid reducing agent in an isolated sample comprising mammal cells. This aspect aims the use of the SHBG as reagent in biochemistry assays in which isolated mammal cells are used to study mechanistic cell processes, metabolic pathways or to test substances in screening methods.

BRIEF DESCRIPTION OF THE DRAWINGS

FIG. 16 shows the amount of HNF-4α and PPARγ protein bound to the human SHBG promoter in the liver of shbg-db/+ and shbg-db/db mice.

FIG. 19 (A) shows in the Y-axis the increasing weight (Weight (W) in grams (g)) along weeks in the X-axis (Time (T) in weeks (w)). FIG. 19 (B) depicts the visceral adipose tissue (VAT in grams (g)) in both animal types and after 12 weeks of fat diet.

FIG. 20 (*a*) to (*c*) show, respectively, in the Y-axis SHBG mRNA levels and protein concentration, and ACC mRNA levels determined in HepG2 cells with control vector (pCMV) and with a vector expressing SHBG (pCMV-SHBG). FIG. 20 (*d*) to (*f*) show, respectively, in the Y-axis SHBG mRNA levels and protein concentration, and ACC mRNA levels determined in HepG2 cells with shvector scramble oligo (shControl) and with a small-hairpin RNA blocking/quenching SHBG expression (shSHBG).

DETAILED DESCRIPTION OF THE INVENTION

Figure 1:
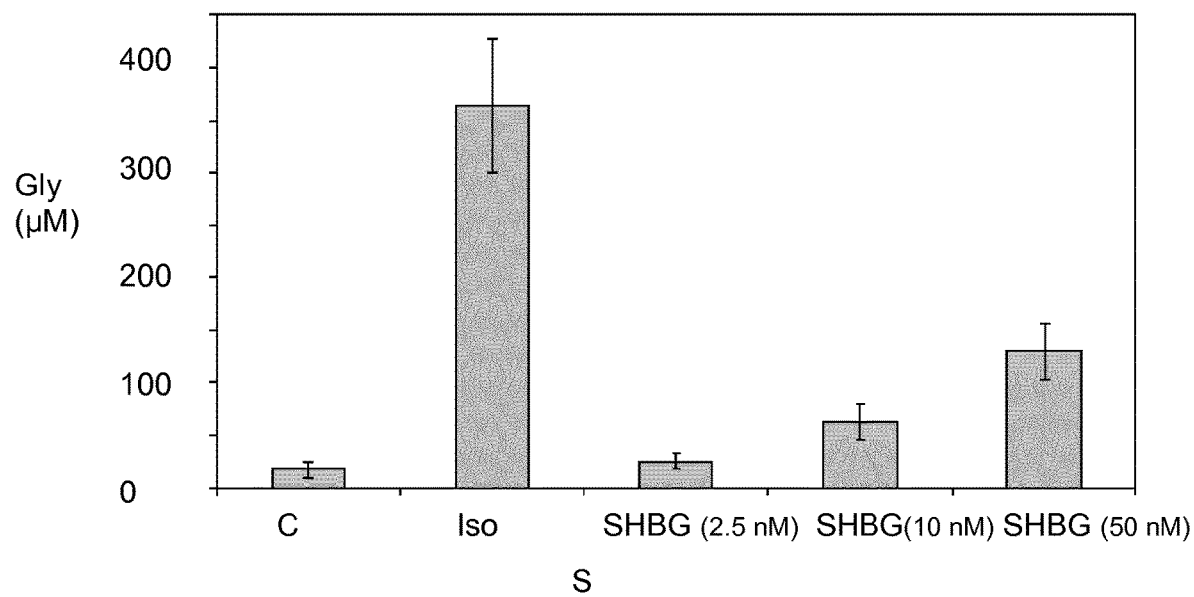
FIG. 1 is a bar diagram that shows in the Y-axis the glycerol (Gly) concentration (μM), for each assayed sample (S) in the X-axis in HepG2 cells. Iso means Isoproterenol; C is the control; SHBG is the sex hormone-binding globulin and the concentration (nM) into brackets is the final concentration in the cell culture.

Following definitions are included in order to facilitate comprehension of the invention.

The expression "for reducing the lipid content in mammal cells", or which is the same "for reducing the lipid accumulation in mammal cells" is to be understood as the fact of lowering the total lipid content in a mammal cell in respect of the initial content before the administration of the SHBG. "Total lipid" includes the content of triglycerides disposed generally in vesicles or granules in the cytoplasm of the cell, and including also the triglycerides disposed in the inner face of the external cell membrane.

By "sex hormone-binding globulin" is to be understood any amino acid sequence comprising the entire sequence of the sex hormone-binding globulin of a mammal, as well as any post-translational modification (i.e. glycosylation, disulfide bonds, lipidations). In the particular case of the human sex hormone-binding globulin it is also encompassed any of the entire isoforms 1 to 5 of the protein, as well as any amino acid sequence with a percentage of homology of at least 80%, preferably 90%, and most preferably 95%, with any of the wild-type human isoforms. Also it is encompassed any amino acid sequence with a percentage of identity of at least 80%, preferably 90%, and most preferably 95% with any of the wild-type human isoforms.

The "percentage of homology" between two amino acid sequences is to be understood as the percentage of the sequence positions identical or replaced with other amino acids with lateral chains of similar features (i.e. polar, non-polar, with amino groups, with —SH groups), according to the broadly accepted classifications known by an expert in the field. The "percentage of identity" between two amino acid sequences is to be understood as the percentage of the sequence positions with identical amino acids. The percentage of homology and of identity between sequences may be calculated by means of "sequence alignment". The sequence alignment may be local or global. In the sense of the present invention the percentage of homology and of identity will be calculated, preferably, over a global alignment, among the entire sequence or an entire active fragment of the sequence. Global alignments are more useful when the sequences are similar and have approximately the same size (long). There are several algorithms available in the state of the art for performing these global alignments. There are also bioinformatics tools using such algorithms to obtain the percentage of identity and homology between sequences. As an example, global alignment between sequences may be performed by means of the well-known GGSEARCH or GLSEARCH software.

For "any fragment of the sex hormone-binding globulin" it is encompassed a subunit of the SHBG, as well as an amino acid sequence comprising from 10 to 200 amino acids isolated from the entire amino acid sequence of the wild-type sex hormone-binding globulin, or isolated from an amino acid sequence with at least a percentage of homology or identity of at least 80%, preferably 90%, and most preferably 95%, with any of the five wild-type human isoforms. The isolated fragment from the entire protein maintains the function of lowering lipid content in an animal cell, as the entire sex hormone-binding globulin. A way to test if the fragment maintains the function can be performed in vitro by adding the fragment of SHBG at different final cell culture concentrations (2.5 nM, 10 nM and 50 nM) in a culture of HepG2 hepatoblastoma cells (catalog no. HB-8065; ATCC) maintained in DMEM supplemented with 10% FBS and antibiotics. For experiments, HepG2 cells are cultured to 60%-80% confluence, washed and incubated with Lipolysis Assay Buffer (Zenbio) containing vehicle (control—C), Isoproterenol (positive control—ISO, 3 µM). After 16 hours incubation, the media iscollected and glycerol concentration is assessed using, for example a Glycerol Detection Kit (Zenbio). If glycerol is detected in a concentration greater than the control, it is to be deduced that the fragment of the SHBG maintains the function as lipid reduction agent in animal cells.

A "lipolytic agent" is a compound that induces lipolysis, which is the enzymatic decomposition of triglycerides into glycerol and fatty acids. Examples of known lipolytic agents include epinephrine, norepinephrine, ghrelin, growth hormone and cortisol.

An "inhibitor of the lipogenesis" is a compound that avoids the formation of triglycerides from the enzymatic condensation of glycerol and fatty acids.

Examples of known inhibitors of lipogenesis include cerulenin.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc., must also be "acceptable" in the sense of being compatible with the other ingredients of the formulation. Suitable carriers, excipients, etc. can be found in standard pharmaceutical texts, and include, as a way of example preservatives, agglutinants, humectants, emollients, and antioxidants.

The term "effective amount" as used herein, means an amount of an active agent high enough to deliver the desired benefit (either the treatment or prevention of the illness), but low enough to avoid serious side effects within the scope of medical judgment.

The term "cosmetically acceptable" or "dermatological acceptable", which is herein used interchangeably, refers to the excipients or carriers suitable for use in contact with human skin without undue toxicity, incompatibility, instability, allergic response, among others As mentioned above, an aspect of the invention relates to sex hormone-binding globulin (SHBG) and/or any fragment thereof for use to reduce lipid content in cells of a mammal in respect of the initial lipid content or the lipid content (before the administration or addition of SHBG, or before putting the cells into contact with SHBG). The cells are those comprising lipids (mostly triglycerides) in droplets, granules or vesicles used as lipid storage by the cells.

Thus, in a particular embodiment, the invention relates to the use of SHBG as defined above for the manufacture of a medicament for reducing lipid content in cells of a mammal, said cells comprising cytoplasm granules, vesicles or droplets comprising triglycerides. The present invention also refers to a method for reducing lipid content in cells of a mammal in need thereof, including a human, said cells comprising cytoplasm granules, vesicles or droplets comprising triglycerides, the method comprising administering a therapeutically effective amount of the SHBG, together with pharmaceutically acceptable excipients and/or carriers.

The reduction of lipid content in animal cells, namely of the triglycerides in the granules, vesicles or droplets of the cytoplasm of the cells, as well as of triglycerides sited at the inner face of the external plasmatic membrane, leads to a reduced mass (or amount) of the global adipose tissue among the body mass of an animal, including a human. The adipose tissue is the connective tissue composed mostly of adipocytes. At the same time, the reduction of the triglycerides takes place in other tissues involved in the lipid metabolism, such as in the liver tissue (hepatocytes).

As will be illustrated by means of the examples below, the SHBG and/or a fragment thereof is able to regulate the lipid metabolism in cells of a mammal (i.e. it is a lipid metabolism regulator) due to its role of lipolytic agent and of lipogenesis inhibitor.

In a preferred embodiment, the mammal cells are selected from the group consisting of hepatocytes and adipocytes.

Adipocytes, also known as lipocytes and fat cells, are the cells that primarily compose adipose tissue, specialized in storing energy as fat. There are two types of adipose tissue, white adipose tissue (WAT) and brown adipose tissue (BAT), which are also known as white fat and brown fat, respectively, and comprise two types of fat cells. White fat cells or monovacuolar cells contain a large lipid droplet surrounded by a layer of cytoplasm. The nucleus is flattened and located on the periphery. A typical fat cell is 0.1 mm in diameter with some being twice that size and others half that size. The fat stored is in a semi-liquid state, and is composed primarily of triglycerides and cholesteryl ester. If excess weight is gained as an adult, fat cells increase in size about fourfold before dividing and increasing the absolute number of fat cells present. Brown fat cells or plurivacuolar cells are polygonal in shape. Unlike white fat cells, these cells have considerable cytoplasm, with lipid droplets scattered throughout. The nucleus is round, and, although eccentrically located, it is not in the periphery of the cell. The brown color comes from the large quantity of mitochondria. Brown fat, also known as "baby fat," is used to generate heat.

After marked weight loss the number of fat cells does not decrease (the cells contain less fat). Fat cells swell or shrink but remain constant in number. However, the number of fat cells may increase once existing fat cells are sufficiently full. However, in some reports and textbooks, the number of fat cell (adipocytes) increased in childhood and adolescence. The total number is constant in both obese and lean adult. Individuals who become obese as adults have no more fat cell than they had before.

A hepatocyte is a cell of the main tissue of the liver. Hepatocytes make up 70-85% of the liver's cytoplasmic mass. These cells are involved in protein synthesis, protein storage, transformation of carbohydrates, synthesis of cholesterol, bile salts and phospholipids, and in the detoxification, modification, and excretion of exogenous and endogenous substances. The hepatocyte also initiates formation and secretion of bile. The liver forms fatty acids from carbohydrates and synthesizes triglycerides from fatty acids and glycerol. Hepatocytes also synthesize apoproteins with which they then assemble and export lipoproteins (VLDL, HDL). In lipid metabolism, the liver receives many lipids from the systemic circulation and metabolizes chylomicron remnants. It also synthesizes cholesterol from acetate and further synthesizes bile salts.

Due to its role of lipolytic agent and inhibitor of lipogenesis, SHBG and/or any fragment thereof can be used for the treatment and/or prevention of overweight, obesity, hepatic steatosis, diabetes or cardiovascular diseases in a mammal. Accordingly, it is also part of the invention the SHBG and/or any fragment thereof for use in the treatment and/or prevention of a disease selected from the group consisting of overweight, obesity, hepatic steatosis, diabetes and cardiovascular diseases in mammals. In a preferred embodiment, the mammal is a human.

This aspect of the invention can also be formulated as the use of SHBG as defined above for the manufacture of a medicament for the treatment and/or prevention of a disease selected from the group consisting of overweight, obesity, hepatic steatosis, diabetes and cardiovascular diseases in mammals, including human. The present invention also relates to a method of treatment and/or prevention of a disease selected from the group consisting of overweight, obesity, hepatic steatosis, diabetes and cardiovascular diseases in mammals, including human, the method comprising administering a therapeutically effective amount of the SHBG, together with pharmaceutically acceptable excipients and/or carriers.

In a preferred embodiment, the SHBG and/or any fragment thereof is for use in the treatment and/or prevention of obesity in mammals. Preferred mammals are humans.

In another preferred embodiment, the SHBG and/or any fragment thereof is for use in the treatment and/or prevention of hepatic steatosis in mammals. Preferably the mammal is a human. This hepatic steatosis may be associated to excessive alcohol intake, to obesity (with or without effects of insulin resistance) or to diabetes, hypertension and dislipidemia (metabolic syndrome).

In a preferred embodiment, the SHBG and/or any fragment thereof for use as disclosed above is preferably a mammalSHBG, including human SHBG.

In another embodiment, the SHBG is an isoform of the human sex hormone-binding globulin comprising the amino acid sequence selected from the group consisting of SEQ ID NO: 1, SEQ ID NO: 2, SEQ ID NO: 3, SEQ ID NO: 4, SEQ ID NO: 5, and mixtures thereof comprising the two, three, four or the five isoforms. These isoforms may include post-translational, as well as peptide fragments (from 10 to 200 amino acids) sited at the N-terminal and/or C-terminal ends of any of SEQ ID NO:1 to 5.

Among the post-translational modifications, there are included O-glycosylations, N-glycosylations, or the lipidation of the SHBG by adding a fatty acid (e.g palmitic or myristic). With regard to the glycosilations, it is to be noted that every subject has at least one O-Glycosylation, and frequently two N-Glycosylated sites. Even some people have a SHBG with three N-Glycosylated sites. It is in addition known that three N-Glycosylated sites reduce the clearance of the SHBG. All these above listed modifications are also encompassed in the SHBG for use according to the invention.

In addition, these isoforms of the human SHBG can be obtained synthetically, or by recombinant technology (i.e. production by DNA recombinant technology in bacteria and yeast). Other source of human SHBG isoforms is by extraction from liver tissue, or from human plasma.

In another embodiment, the SHBG for use according to the invention, consists in an isoform of the human sex hormone-binding globulin selected from the group consisting of SEQ ID NO: 1, SEQ ID NO: 2, SEQ ID NO: 3, SEQ ID NO: 4, SEQ ID NO: 5, and mixtures thereof comprising the two, three, four or the five isoforms. These isoforms may include the post-translational modifications disclosed above, as well as any peptide fragments (from 10 to 200 amino acids) sited at the N-terminal and/or C-terminal ends.

The SHBG and/or a fragment thereof for use according to the invention, may be externally administered (parenteral, oral, topically). In addition, it can be administered as a gene therapy in the form of a nucleic acid construct able (vector) to reach hepatic cells and to express the protein under induction. This gene therapy can be done by the use of viral vectors (e.g Retrovirus vectors, Adenovirus vectors, Adeno-Associated virus vectors, Herpes Simplex Virus vectors, Lentivirus, etc.) expressing SHBG under the control of liver specific promoters and/or strong constitutive promoters (e.g CMV). Gene therapy can also be done by the use of non-viral methods of DNA transfer, such as naked DNA, liposomes or molecular conjugates. When gene therapy is employed, and in the particular case of human SHBG, it can be administered a gene construct that gives rise to the five isoforms by means of the alternative splicing, or that only gives raise to one of them or to some of them.

Thus, in an embodiment of the invention the SHBG and/or any fragment thereof can be conveniently administered to a patient.

With this purpose, the SHBG and/or any fragment thereof for use according to the invention is, in a particular embodiment, an ingredient of a pharmaceutical composition comprising an effective amount of the SHBG and/or any fragment thereof, in combination with pharmaceutically acceptable excipients and/or carriers. Thus, SHBG and/or any fragment thereof for use of the present invention can be in form of a pharmaceutical composition comprising an effective amount of SHBG and/or any fragment thereof in combination with pharmaceutically acceptable excipients or carriers. This aspect can also be formulated as a pharmaceutical composition comprising an effective amount of SHBG and/or any fragment thereof, in combination with pharmaceutically acceptable excipients or carriers for use to reduce the lipid content in mammal cells.

In another embodiment, the pharmaceutical composition comprising an effective amount of SHBG and/or any fragment thereof, in combination with pharmaceutically acceptable excipients or carriers, is for use in the treatment and/or prevention of a disease selected from the group consisting of overweight, obesity, hepatic steatosis, diabetes and cardiovascular diseases in a mammal, including a human. This means that the SHBG and/or any fragment thereof, is used to prepare a pharmaceutical composition for the treatment and/or prevention of a disease selected from the group consisting of overweight, obesity, hepatic steatosis, diabetes and cardiovascular diseases in a mammal. This can also be formulated as a method of treatment and/or prevention of a disease selected from the group consisting of overweight, obesity, hepatic steatosis, diabetes and cardiovascular diseases in mammals, including human, the method comprising administering a pharmaceutical composition comprising a therapeutically effective amount of the SHBG, together with pharmaceutically acceptable excipients and/or carriers.

In a preferred embodiment, the SHBG and/or any fragment thereof for use according to the invention is an ingredient of (or forms part of) a pharmaceutical composition for parenteral administration. Thus, the pharmaceutical composition for use according to the invention is a parenteral composition.

In another embodiment the pharmaceutical composition for use according to the invention and comprising the SHBG and/or any fragment thereof is a composition for oral administration.

The invention also encompasses the use of a cosmetically effective amount of SHBG and/or any fragment thereof, for improving the bodily appearance of a mammal with subcutaneous fat herniated or accumulated within the fibrous connective tissue under the skin. This aspect can also be formulated as a cosmetic method for improving the bodily appearance of a mammal with subcutaneous fat herniated or accumulated within the fibrous connective tissue under the skin comprising administering a cosmetically effective amount of SHBG and/or any fragment thereof, together with cosmetically excipients or carriers.

Subcutaneous fat is found just beneath the skin, as opposed to visceral fat, which is found in the peritoneal cavity. Subcutaneous fat can be measured using body fat calipers giving a rough estimate of total body adiposity. This fat aids in the process of homeostasis, by forming a layer of insulation to slow heat loss.

The fibrous connective tissue is the fraction containing fibroblasts cells and extracellular matrix components from the hypodermis (or connective tissue). The whole connective tissue also comprises adipose cells and macrophages. The hypodermis is used mainly for fat storage.

Thus, in a particular embodiment the cosmetic use is for a mammal with cellulite.

In another embodiment, the cosmetically effective amount of SHBG and/or any fragment thereof is an ingredient of a cosmetic topical composition in combination with acceptable cosmetically excipients and/or carriers. Thus, SHBG and/or any fragment thereof for improving the bodily appearance of a mammal with subcutaneous fat can be in form of a topical cosmetically composition comprising a cosmetically effective amount of SHBG and/or any fragment thereof, in combination with acceptable cosmetically excipients and/or carriers.

This aspect can also be formulated as use of a topical cosmetic composition comprising an effective amount of SHBG and/or any fragment thereof, in combination with cosmetically acceptable excipients or carriers for improving the bodily appearance of a mammal with subcutaneous fat herniated or accumulated within the fibrous connective tissue under the skin.

In particular, the cosmetic effect of the SHBG and/or any fragment thereof derives from being a lipolytic agent, as well as an inhibitor of lipogenesis in animal (mammal) cells. Therefore, the topical administration of SHBG and/or a fragment thereof leads to the reduction of the subcutaneous fat herniated or accumulated within the fibrous connective tissue, or which is the same, reduces cellulite manifested topographically as skin dimpling and nodularity, often on the pelvic region (specifically the buttocks), lower limbs, and abdomen in females. In males, also comprising subcutaneous fat entrapped within fibrous connective tissue, the SHBG and/or a fragment thereof acts as the so-called cosmetically reducing agent.

In a preferred embodiment, the cosmetic composition is topically administered in the desired areas of the body. The topical compositions of the invention can be formulated in several forms that include, but are not limited to, solutions, aerosols and non-aerosol sprays, shaving creams, powders, mousses, lotions, gels, sticks, ointments, pastes, creams, shampoos, shower gel, body washes or face washes.

In yet another embodiment, the SHBG used in a cosmetically effective amount is preferably a mammal SHBG, including human SHBG. In a preferred embodiment the SHBG is an isoform of the human SHBG comprising the amino acid sequence selected from the group consisting of SEQ ID NO: 1, SEQ ID NO: 2, SEQ ID NO: 3, SEQ ID NO: 4, SEQ ID NO: 5, and mixtures thereof comprising the two, three, four or the five isoforms. These isoforms may include the post-translational modifications disclosed above, as well as any peptide fragments (from 10 to 200 amino acids) sited at the N-terminal and/or C-terminal ends.

The cosmetic use of the SHBG and/or a fragment thereof according to the invention is for the application in mammals, in particular in humans, which are healthy subjects that need not have any diseases. That is, they can be subjects without obesity, overweight or not suffering fatty liver. The cosmetic use is only for esthetical purposes aiming to improve the bodily appearance, and not to treat any disease. In general terms, the cosmetically effective amounts are different than therapeutically effective amounts, since in a cosmetic use the SHBG and/or fragment thereof has only to reach the fat accumulated or stored at subcutaneous level.

Indeed, due to its role as lipolytic agent (and as inhibitor of lipogenesis), the SHBG and/or a fragment thereof can also be used to reduce the lipids (mass of adipose tissue) that accumulate in many parts of the animal body. In the particular case of the human body, the lipid accumulation (adipose tissue with high amounts of triglycerides) tends to accumulate in the hips, waist, abdomen, and thighs. As will be illustrated in the examples below, the SHBG or a fragment thereof reduces the triglyceride contents in adipocytes (as well as the adipocyte size), thus leading to a reduction of the accumulated lipid along the body.

The compositions according to the invention, which are pharmaceutical or cosmetic compositions, comprise pharmaceutically or cosmetically excipients and/or carriers selected from the group consisting of a solvent or vehicle, a viscosity agent, a hydrating agent, a gelling agent, an emollient, a pH-regulating agent, an antioxidant, a preservative agent, and a mixture thereof.

Finally, when the SHBG and/or any fragment thereof is for use as lipid reducing agent in an isolated sample comprising mammal cells, preferred cells are selected from the group consisting of adipocytes and hepatocytes.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Low plasma SHBG levels are associated with obesity but there are no studies addressing the question of whether SHBG could play an active role in the development of obesity. To shed light to this issue the inventors created a double transgenic mouse that expresses the human SHBG and develops obesity.

The following examples illustrate the lipolytic effect of SHBG, as well as its role as inhibitor of lipogenesis in animal cells. In vitro experiments have shown that SHBG produces lipolysis in human mature adipocytes and in human hepatocytes. In addition in vivo experiments have shown that SHBG reduces total body weight, fat accumulation, lipid accumulation in hepatocytes (hepatic steatosis) and inflammation. Therefore, SHBG can be for use as a medicament, in particular as a medicament to treat obesity and other associated complications including hepatic steatosis, diabetes and cardiovascular diseases. The medicament is for reducing lipid accumulations or contents in respect of the initial content in mammal cells.

Example 1

SHBG Causes Lipolysis in Human Hepatocytes

Cell culture experiments. Cell culture reagents were from Life Technologies Inc (Invitrogen SA). HepG2 hepatoblastoma cells (catalog no. HB-8065; ATCC) were maintained in DMEM supplemented with 10% foetal bovine serum (FBS) and antibiotics. For experiments, HepG2 cells were cultured to 60%-80% confluence, cells were washed and incubated with Lipolysis Assay Buffer containing vehicle (control—C), Isoproterenol (positive control—ISO, 3 µM) or SHBG at different final cell culture concentrations (2.5 nM, 10 nM and 50 nM). SHBG was from native human protein purified from healthy human serums (it included the amino acid sequence SEQ ID NO: 1). After 16h incubation, media was collected and glycerol concentration was assessed using a Glycerol Detection Kit (Zenbio).

The data are depicted in FIG. 1, wherein the bars indicate the levels of glycerol (Gly) for each assayed sample. Glycerol is a direct measure of the lipolysis level, since is the product obtained when triglycerides are decomposed chemically or enzymatically to glycerol and fatty acids.

As can be seen in this FIG. 1 increasing levels of SHBG increased the lipolysis in HepG2 cells (in a dose-dependent manner). Isoproterenol (Iso) is commonly used in these kind of experiments as positive control because it is known that it induces lipolysis.

Example 2

SHBG Causes Lipolysis in Human Adipocytes

A similar in vitro experiment as in Example 1 was performed but using human mature adipocytes from obese subjects instead of the HepG2 cells.

The cells were maintained in DMEM supplemented with 10% foetal bovine serum (FBS) and antibiotics, cultured to confluence, washed and incubated with Lipolysis Assay Buffer containing vehicle (control—C), Isoproterenol (positive control—ISO, 3 µM) or SHBG at different final cell culture concentrations (10 nM and 30 nM). SHBG was from native human protein purified from healthy human serums (it included the amino acid sequence SEQ ID NO: 1). After 16h incubation, media was collected and glycerol concentration was assessed using a Glycerol Detection Kit (Zenbio).

Figure 2:
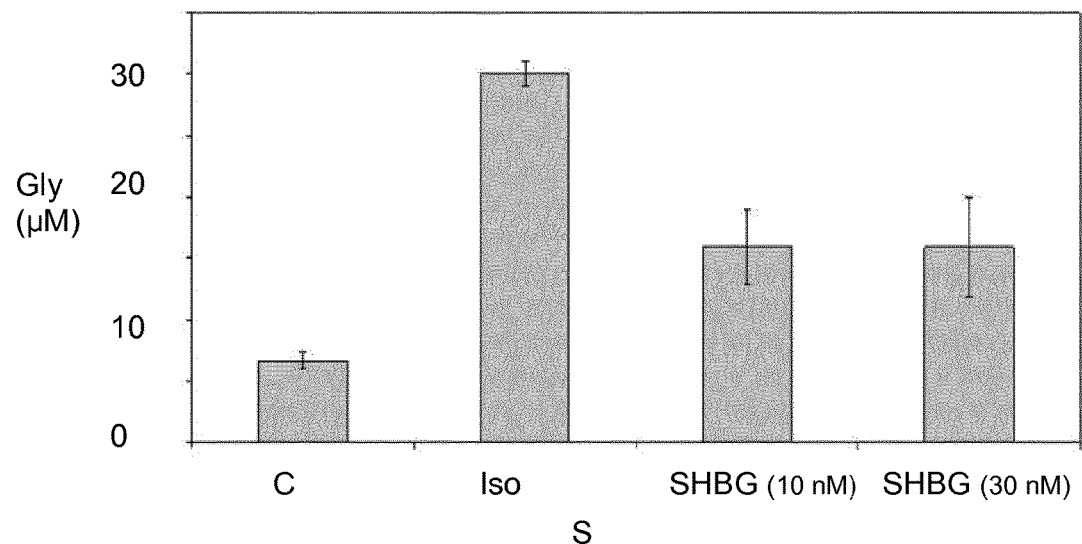
FIG. 2 also shows a bar diagram for the lipolysis assay as in FIG. 1, but performed in adipocytes.

The results in FIG. 2 also show that the bars corresponding to the samples in which SHBG (10 nM and 30 nM, respectively, from the same source as in Example 1) was added were higher than that of the control (C, buffer). Thus, in the samples with mature adipocytes stimulated with SHBG final glycerol concentration was greater than the observed in the non-treated mature adipocytes.

In conclusion, and as derivable from Examples 1 and 2, the treatment of human cells with SHBG was able to reduce mature adipocytes and hepatocytes lipid content by increasing lipolysis and increasing glycerol accumulation in the cell culture medium with respect to the untreated mature adipocytes or HepG2 cells.

Example 3

In Vivo Experiments in Transgenic Mice Overexpressing Human shbg Gene 3.1. Generation of Transgenic Obese Diabetic Mice Overexpressing Human shbg Gene.

Since rodents do not express SHBG in their livers all the available obese-prone rodent models cannot be used to study if SHBG has a role in the development and progression of obesity.

To shed light to this issue, the inventors developed a unique mouse model that expresses the human SHBG gene and develops obesity, by crossing the human SHBG transgenic mice with the db/db mice.

The human SHBG transgenic mice is the one disclosed by Jänne et al, "Human Sex-Hormone-Binding Globulin Gen Expression in Transgenic Mice", Molecular Endocrinology—1998, Vol. No. 12 (1), pp: 123-136.

Briefly, these mice were obtained by microinjecting into the pronuclei of a one-cell mouse embryos, a 4.3 kb portion of a human shbg that comprises the 8 exons of the SHBG plus 0.9 kb 5' of the translation initiation codon in exon 1 and 0.5 kb 3' from the polyadenylation sequence in exon 8. The one-cell embryos were obtained superovulating CBA× C57BL6 hybrid females with pregnant mare serum and hCG (Sigma Chemical Co. Mississauga, Canada) and mating them with CBA×C57BL6 males. Female CD-1 mice were used to produce pseudopregnant recipients by mating with vasectomized CD-1 males. Injected embryos were implanted into the pseudopregnant recipient mice using a standard protocol. This human transgenic mice over expresses the human shbg gene in vivo. According to Northern blot analysis, the human shbg transcripts are most abundant in liver and kidney. At the cellular level, the human shbg transgenes are expressed in clusters of hepatocytes located mainly within the periportal region of hepatic lobules and in the epithelial cells lining the proximal convoluted tubules of the kidney. This results in high levels of human SHBG in serum and urine of mature male shbg mice.

The db/db mice corresponds to the JAX™ Mice Strain: Diabetic Mice db/db (from Charles River; www.criver.com/en-US/Pages/home.aspx). These mice are characterized by having a point mutation in the leptin receptor. In homozygosis the lack of leptin signaling in the hypothalamus will lead to persistent hyperphagia, obesity, type 2 diabetes, dyslipidaemia and fatty liver. In this mice, diabetes (db), which occurred in an inbred strain of mouse, is inherited as a unit autosomal recessive and is characterized by a metabolic disturbance resembling diabetes mellitus in man. Abnormal deposition of fat at 3 to 4 weeks of age is followed shortly by hyperglycemia, polyuria, and glycosuria. Accompanying morphological changes in the islets of Langerhans suggest neogenesis to compensate for insulin depletion.

These manifestations are apparent at 4-6 week of age and death occurs at approximately 5-8 months of age.

The characterization of the SHBG-db/db mice (herewith referred also as shbg-db/db) allowed to discover novel actions of SHBG, since the presence of SHBG protects partially against weight gain, reduces fatty liver, fat accumulation and inflammation, as well as, the molecular mechanisms by which SHBG is down regulated during obesity development.

For performing the assays, mice were maintained under standard conditions with food (Global Diet 2018, Harlan Interfauna Iberica, Barcelona, Spain) and water provided ad libitum and a 12 h light/dark cycle. Experimental procedures were approved by the Institutional Animal Use Subcommittees of Hospital Vall d'Hebron Research Institute and the Universitat Autònoma Barcelona.

The mice for experiments in next illustrated assays were of the following four genotypes:
  db/+, which means lean mice heterozygous at point mutation in the leptin receptor.
  db/db, which means that the mice were homozygous for the point mutation in the leptin receptor and behave a phenotype of persistent hyperphagia, obesity, type 2 diabetes, dyslipidaemia and fatty liver,
  shbg-db/+ lean mice heterozygous at point mutation in the leptin receptor and expressing the shbggene
  shbg-db/db, which means that the they over-expressed shbg gene in the manner disclosed above and at the same time they had the phenotype of the homozygous db/db mice in relation to hyperphagia, obesity, type 2 diabetes, dyslipidaemia and fatty liver.

Materials and methods for in vivo experiments.

Histology and Immunohistochemistry: For morphological studies, 3 animals of each genotype (db/+, db/db, shbg4-db/+ and shbg4-db/db) were used. Livers and adipose tissue were fixed in 4% paraformaldehyde for 24 h and embedded in paraffin. Serial 5-μm thick sections were used for histological examination and stained with hematoxylin-eosin (H&E).

For immunohistochemistry studies, the paraffin sections were de-waxed and incubated at high power in a microwave oven for 10 min in citrate buffer, pH 6.6. The sections were then cooled at room temperature for 20 min and treated with a 0.03% hydrogen peroxide solution for 7 min, prior to incubation (overnight at 4° C.) with rabbit antibodies against F4/80. The immunoreactiveF4/80 was detected using the EnVision™ +System, HRP (DAB) from DAKO (Carpinteria, Calif.).

3.2. SHBG Reduces Weight Gain but not Blood Glucose Levels During the Development of Obesity in Human shbg-db/db Transgenic Mice.

One set of male mice of the four genotypes (db/+, db/db, shbg-db/+ and shbg-db/db) n=5 each were followed up to 12 weeks assessing weight and blood glucose every two weeks. Blood samples were taken by saphenous vein for measurements of plasma SHBG levels every two weeks. Another set of male mice of each genotype (n=5) was sacrificed at 6 weeks of age and blood and tissues (liver, kidney, testis, fat pad) were collected and weighted for RNA and protein isolation.

Figure 3:
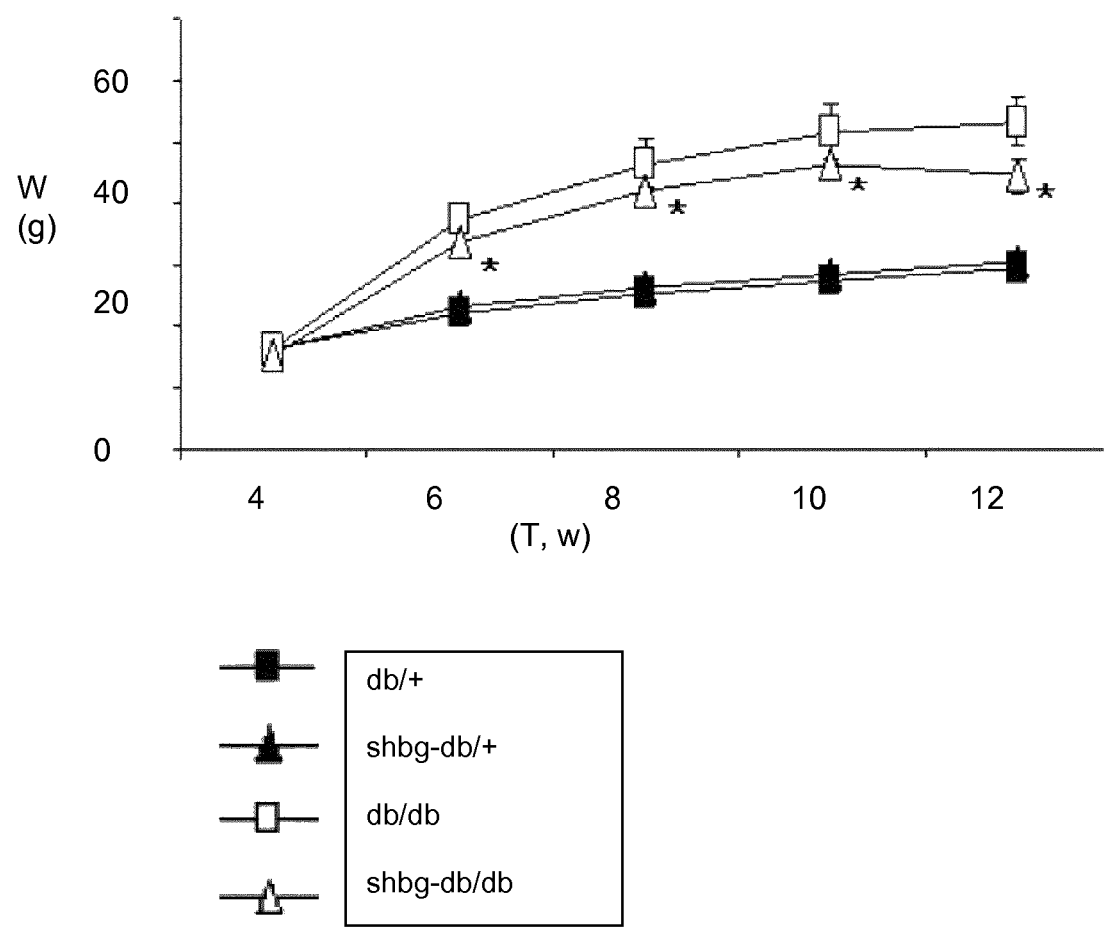
FIG. 3 is a graphic that shows the Body weight (W in grams (g)) in mice (n=5) among time (T in weeks (w)) for each assayed genotype: lean mice db/+ (black square) and lean mice shbg-db/+ (black triangle); obese mice shbg-db/db (white triangle) and obese mice db/db (white square).

Body weight and blood glucose were assessed in mice (n=5) of each different genotype (lean: db/+ and shbg-db/+; obese: db/db and shbg-db/db) every two weeks from four weeks of age until 12 weeks. The results are depicted in FIG. 3, wherein it is indicated the weight of the mice (W in grams g)) along the measuring time (T in weeks (w)). These results showed that obese db/db and shbg-db/db mice had increasingly higher weight than their lean db/+(black square) and shbg-db/+(black triangle) littermates from 6 weeks of age until week 12 However, shbg-db/db (white triangle) mice showed a significant reduction in body weight when compared with db/db (white square) mice.

3.3. SHBG Reduces Adipose Tissue Weight and Adipocyte Size in Human shbg-db/db Transgenic Mice. Analysis of Fat Accumulation (VAT)

Visceral adipose tissue was removed from the mice and weighted in a precision balance.

It was also determined the adipose tissue weight and histology in mice (n=3) of each different genotype (lean: db/+ and shbg-db/+; obese: db/db and shbg-db/db) sacrificed at 6 weeks.

Figure 4:
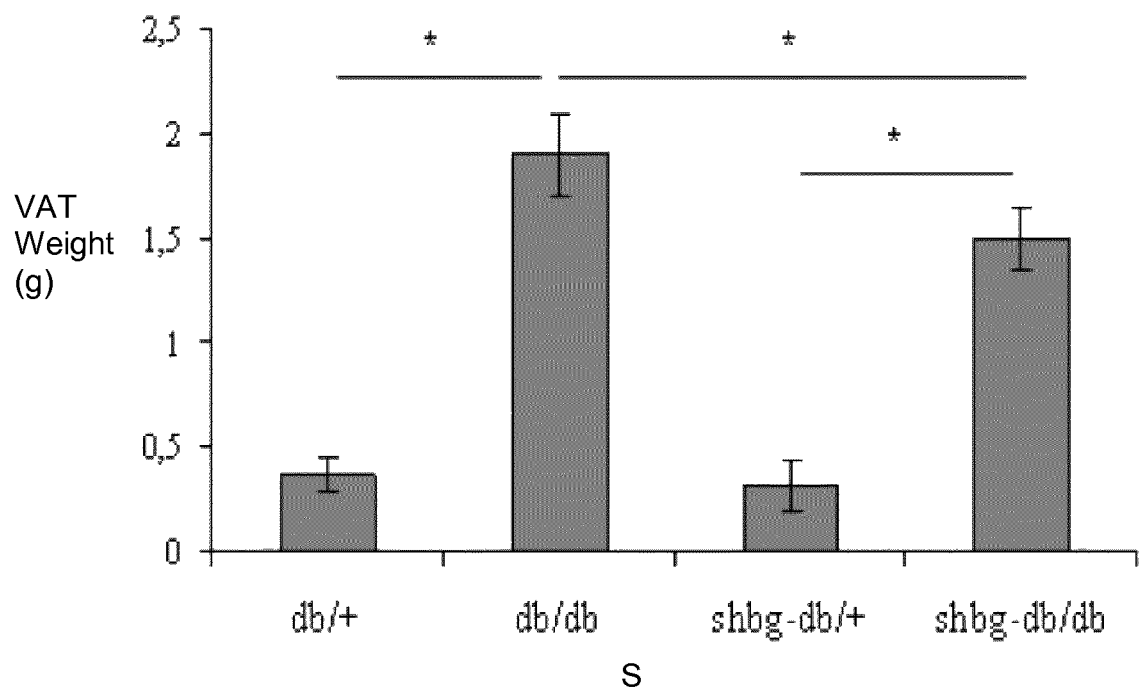
FIG. 4 is a bar diagram with the VAT Weight (VAT=Visceral Adipose Tissue) in grams (g) in the Y-axis determined in each assayed sample (S in the X-axis) or genotype: obese diabetic mice (db/db), obese diabetic expressing human SHBG (shbg-db/db) mice, lean db/+ mice and shbg-db/+ lean mice.

As can be deduced from FIG. 4, which is a bar diagram showing the Visceral adipose tissue(VAT) in grams determined in each genotype, a significantly increased in adipose tissue weight of obese db/db and shbg-db/db mice when compared with lean db/+ and shbg-db/+ mice was observed. However, again shbg-db/db mice had significantly reduced adipose tissue weight when compared with db/db mice.

Figure 5:
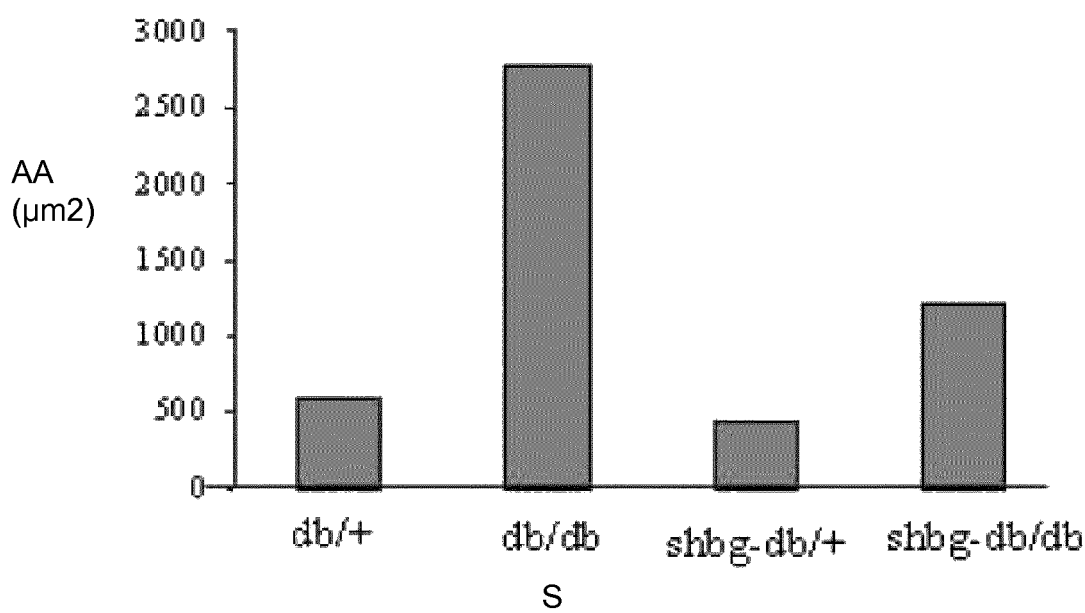
FIG. 5 shows the adipocyte area (AA in µm$^2$) determined for each genotype or sample type (S) as in FIG. 4. The adipocyte area is measured using the ImageJ program (imagej.softonic.com), which is a public domain software for the processing of digital imaging, programmed in Java and developed by the National Institute of Health (NIH).

Histological examreation and quantification of the adipose tissue from these mice revealed that obese db/db and shbg-db/db had bigger adipocyte size when compared with lean db/+ and shbg-db/+ mice. However, shbg-db/db mice had smaller adipocyte size than db/db mice. This later histological examination is summarized in FIG. 5. This figure shows the adipocyte area ($\mu m^2$) determined for each genotype or sample type. The adipocyte area is measured using the ImageJ program (imagej.softonic.com).

3.4. SHBG Reduces Liver Weight and Hepatic Steatosis by Reducing Hepatic Lipogenesis in shbg-db/db Transgenic Mice.

Figure 6:
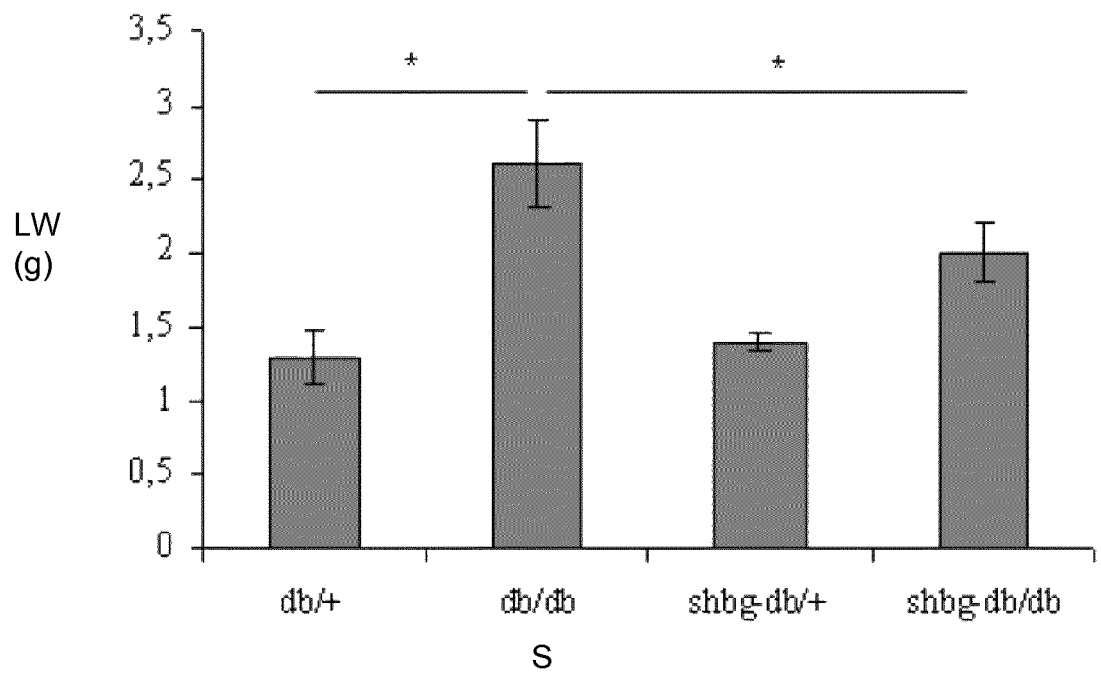
FIG. 6 exposes in the Y-axis the liver weight (LW in grams (g)) (n=3) of each different genotype or sample (S) (lean: db/+ and shbg-db/+; obese: db/db and shbg-db/db) sacrificed at 6 weeks.

It was further analyzed the liver weight and histology in mice (n=3) of each different genotype (lean: db/+ and shbg-db/+; obese: db/db and shbg-db/db) sacrificed at 6 weeks, and as indicated above. The results, depicted in FIG. 6, showed a significantly increased in liver weight of obese db/db and shbg-db/db mice when compared with lean db/+ and shbg-db/+ mice. Importantly, shbg-db/db mice had significantly reduced liver weight when compared with db/db mice. In FIG. 6 LW (g) means Liver weight in grams.

The graphic is a bar diagram showing, for each type of tested samples, the total liver weight (LW) measured once sacrificed at 6 weeks of age.

Figure 7:
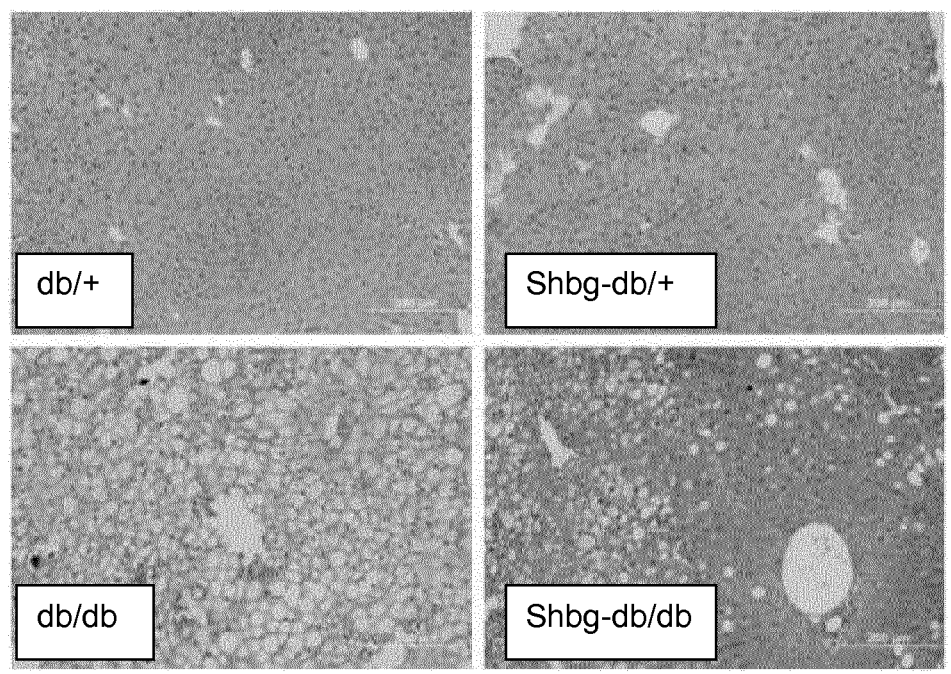
FIG. 7 shows Microscope Images (Olympus-BX61) of a paraffin section further incubated with rabbit antibodies against F4/80 (macrophage marker) of the four studied genotypes (db/+, shbg-db/+, db/db,shbg-db/db).

Histological analysis of livers from these mice, illustrated in FIG. 7, revealed that lean db/+ and shbg-db/+ mice showed normal histology, while obese db/db and shbg-db/db had an important lipid accumulation in their hepatocytes. This can be derived from FIG. 7, wherein a Microscope Image (Olympus-BX61) of a paraffin section further incubated with rabbit antibodies against F4/80 (macrophage marker) of the four genotypes is illustrated. The lipid accumulation in the cells of obese mice (db/db and shbg-db/db) can be seen with the light (white) areas into the cells (Olympus-BX61) However, and also derivable form FIG. 7, shbg-db/db mice had less hepatic steatosis than db/db mice (less white areas—accumulated fat). Interestingly, this improvement in hepatocyte lipid accumulation observed in shbg-db/db mice was predominantly located in the areas around the central vein of liver lobules.

It has been previously described that obese db/db mice had increased lipogenesis when compared with lean db/+ mice after weaning. Therefore it was determined if shbg-db/db mice had lower hepatic lipogenesis than db/db mice. To do so, the mRNA and protein levels of acetyl-CoA carboxylase (ACC) and fatty acid synthase (FAS), two important enzymes that regulate hepatic lipogenesis in mice (n=3) of each different genotype (lean: db/+ and shbg-db/+; obese: db/db and shbg-db/db) were determined. Data from this analysis are illustrated in FIGS. 8 and 9.

Figure 8:
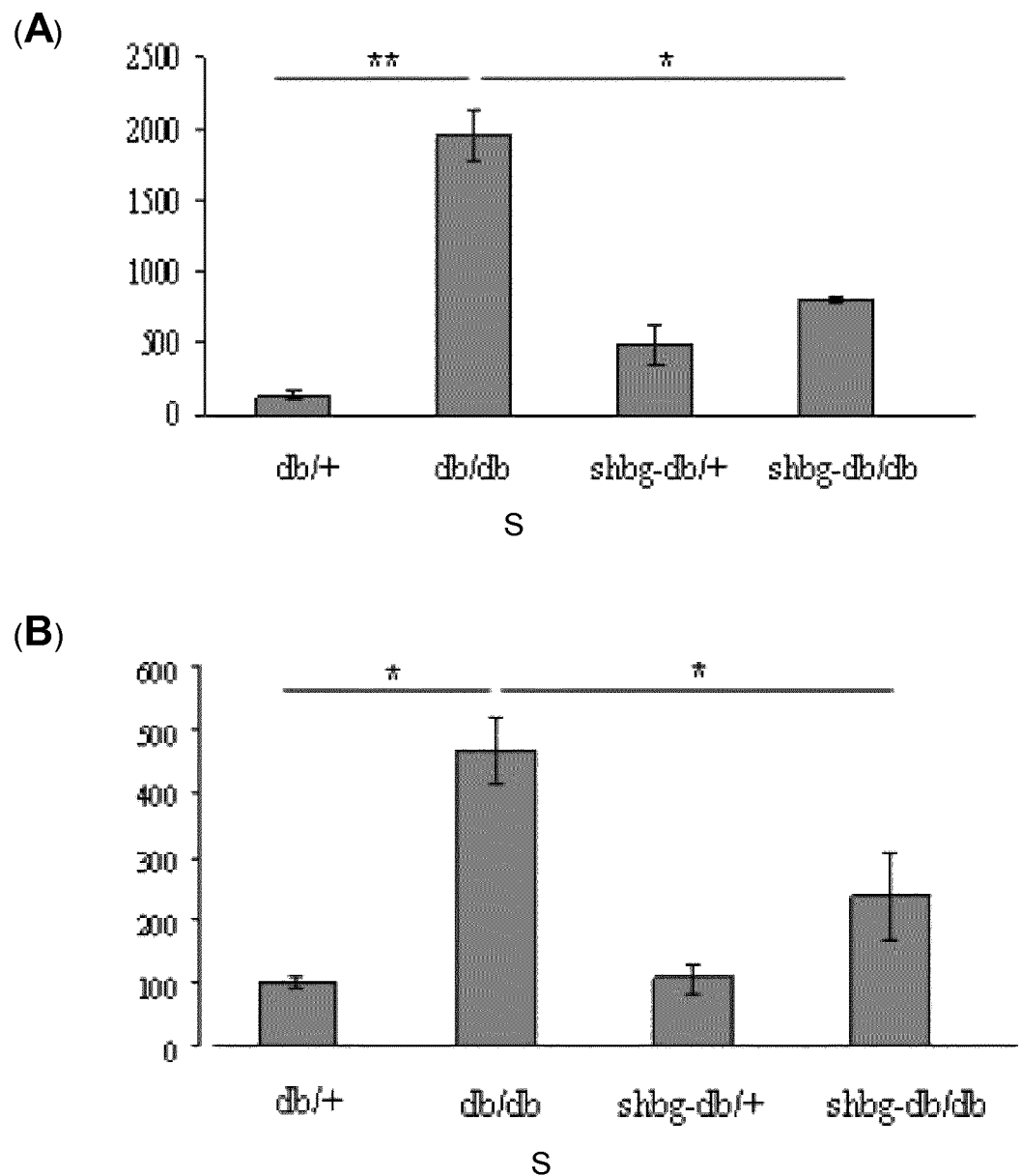
FIG. 8 panels A and B show bar diagrams indicating (Y-axis) the mRNA levels of acetyl-CoA carboxylase (ACCα) (Arbitrary units relative to 18S mRNA levels) (panel A) and fatty acid synthase (FAS) (Arbitrary units relative to 18S mRNA levels) (panel B) for each sample type (S; assayed genotype in the X-axis).
Figure 9:
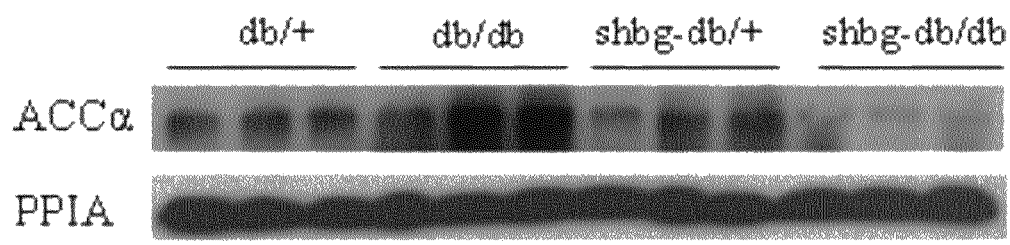
FIG. 9 depicts the protein analysis of mouse livers samples (S) of each genotype. Panel A shows protein levels of ACCα and panel B the protein levels of FAS. PPIA (control) is Peptidylprolylisomerase A. db/+, shbg-db/+, db/db and shbg-db/db have the same meaning as indicated before.
Figure 9:
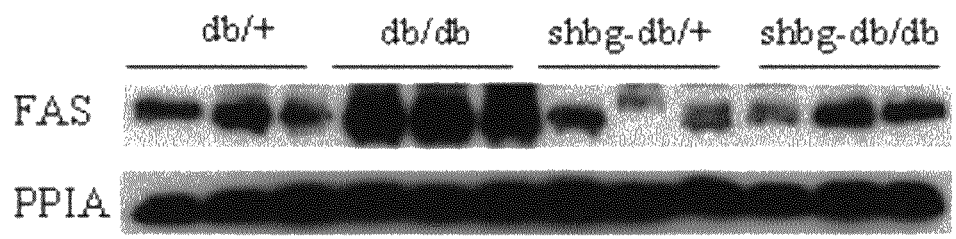

FIG. 8 panels A and B show bar diagrams indicating (Y-axis) the mRNA levels of ACC (panel A) and FAS (panel B) for each sample type (assayed genotype). For the mRNA analysis, total RNA was extracted from mouse livers and adipose tissue samples using TRIzol reagent (Invitrogen SA). Reverse transcription (RT) was performed at 42° C., for 50 min using 3 µg of total RNA and 200 U of Superscript II together with an oligo-dT primer and reagents provided by Invitrogen. An aliquot of the RT product was amplified in a 25-µl reaction using SYBR Green (Invitrogen SA) with appropriate oligonucleotide primer pairs corresponding to mouse ACCα and mouse FAS. Results were analyzed using the 7000 SDS program.

```
Primers for ACC (in 5'-3' direction):
                                    (SEQ ID NO: 7)
Forward, GCCATTGGTATTGGGGCTTAC;

(SEQ ID NO: 8)
Reverse, CCCGACCAAGGACTTTGTTG

Primers for FAS (in 5'-3' direction):
                                    (SEQ ID NO: 9)
Forward, GGCATCATTGGGCACTCCTT;

(SEQ ID NO: 10)
Reverse, GCTGCAAGCACAGCCTCTCT.
```

The results showed that obese db/db and shbg-db/db mice had significantly higher ACC and FAS mRNA levels than when compared with lean db/+ and shbg-db/+ mice. However, shbg-db/db mice had significantly lower ACC and FAS mRNA levels when compared with db/db mice.

The protein analysis is depicted in FIG. 9 (panels A and B). For this purpose, mouse livers samples were homogenized in RIPA (Radioimmunoprecipitation assay buffer) buffer with Complete™ protease inhibitor cocktail (Roche Diagnostics, Barcelona, Spain). Protein extracts were used for western blotting with antibodies against FAS (catalog 22759, Abcam, Cambridge, UK), ACCα (catalog 63531, Abcam) and PPIA (Peptidylprolylisomerase A) (SA-296; BIOMOL Int., Madrid, Spain). Specific antibody-antigen complexes were identified using the corresponding HRP-labeled rabbit anti-goat IgG, rabbit anti-mouse IgG or goat anti-rabbit IgG and chemiluminescent substrates (Millipore) by exposure to x-ray film.

As can be deduced from FIG. 9 (panel A), ACC protein levels were significantly increased in obese db/db when compared with lean db/+ and shbg-db/+ mice while shbg-db/db had reduced ACC protein levels. Furthermore, from FIG. 9 (panel B) it is derivable that FAS protein levels were significantly increased in obese db/db and shbg-db/db mice when compared with lean db/+ and shbg-db/+ mice. However, shbg-db/db mice had significantly lower FAS protein levels when compared with db/db mice.

As a whole, these results showed that SHBG-db/db mice had a reduction in these two key enzymes of hepatic lipogenesis, suggesting that SHBG presence reduces liver fat accumulation by reducing lipogenesis Additionally, total triglyceride content from livers of each genotype (lean: db/+ and shbg-db/+; obese: db/db and shbg-db/db) was also determined (data not shown) and found that lean mice db/+ and shbg-db/+ had less triglyceride content than their obese littermates db/db and shbg-db/db. However, shbg-db/db mice had less triglyceride accumulation than db/db mice.

The results are depicted in next Table 1.

TABLE 1

| Triglyceride amounts (in nanomols of trycglyceride (TG) per grams (g) of tissue) | | |
|---|---|---|
| Genotype | Nmol TGs/ tissue g | Statistical significance |
| db/+ | 74.99 ± 4.17 | [db/+]vs[db/db] p < 0.0001 |
| shbg-db/+ | 88.88 ± 12.84 | [db/+]vs[shbg-db/+] p < 0.0655 |
| db/db | 421.92 ± 58.6 | [db/+]vs[shbg-db/db] p < 0.0001 |
| shbg-db/db | 314.64 ± 41.37 | [db/db]vs[shbg-db/db] p < 0.0002 |
| | | [db/db]vs[shbg-db/db] p < 0.0215 |
| | | [shbg-db/+]vs[shbg-db/db] p < 0.0002 |

3.5 SHBG Lowers Inflammation in shbg-db/db Transgenic Mice

Since obesity is characterized, among other features, by a low-grade inflammation state, it was determined if there were any differences in inflammation between db/db and shbg-db/db mice. The macrophage infiltration in the liver and adipose tissue was first investigated by performing an immunohistochemistry using antibodies against F4/80, a well-known macrophage marker.

Figure 10:
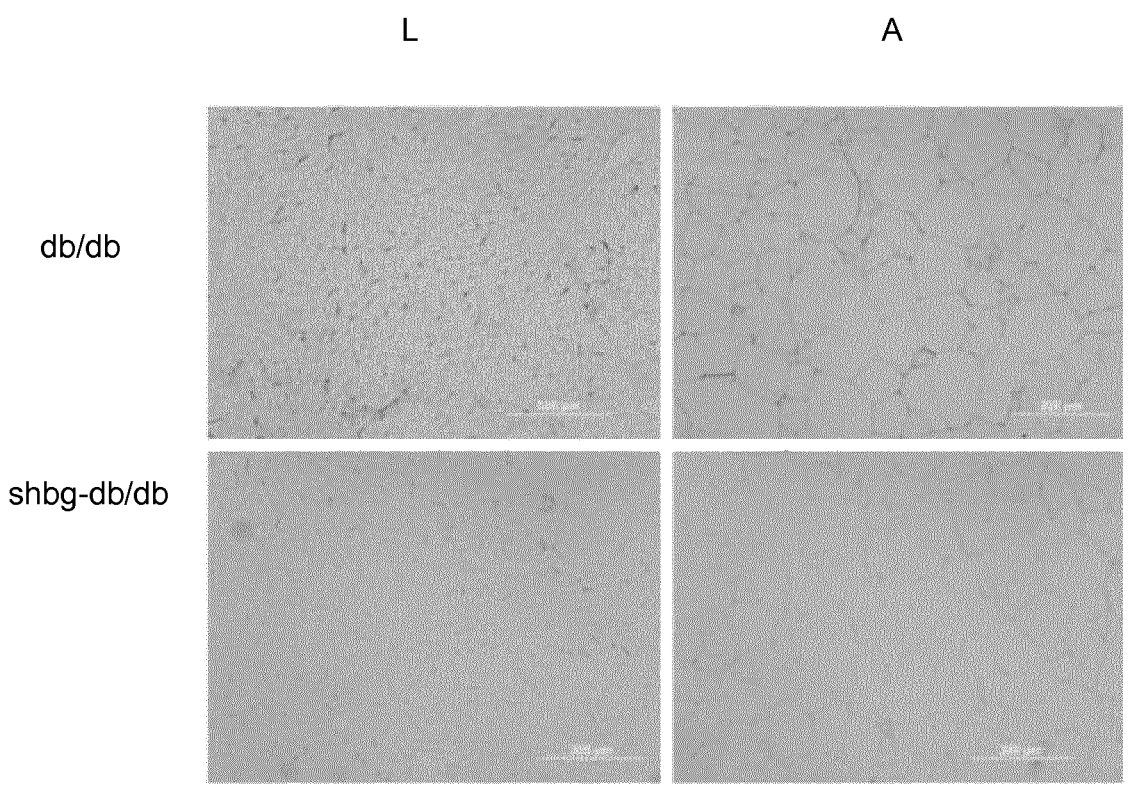
FIG. 10 depicts microscope images (Olympus-BX61) of liver (L) and adipocyte tissue (A) of two assayed genotypes (db/db, and shbg-db/db). Upper images show the results in db/db mice. Lower images show the results in shbg-db/db mice. Images show immunohistochemistry labeling against F4/80 (macrophage marker).

For this analysis, the immunochemistry method disclosed above was applied in paraffin liver sections and adipose tissue sections. The data are depicted in FIG. 10, which shows microscope images (Olympus-BX61) of both tissues, liver (L) and adipocyte tissue (A) for the two assayed genotypes (db/db, and shbg-db/db). Upper images show, respectively, the results in db/db mice in liver (L, in the left of FIG. 10) and adipocyte tissue (A, in the right of FIG. 10). Lower images show, respectively, the results in shbg-db/db mice in liver (L, in the left of FIG. 10) and adipocyte tissue (A, in the right of FIG. 10).

The analysis showed that shbg-db/db mice had less macrophage infiltration in both liver and adipose tissue than db/db mice, as can be deduced from the lower dark staining observable in the lower images of FIG. 10.

Figure 11:
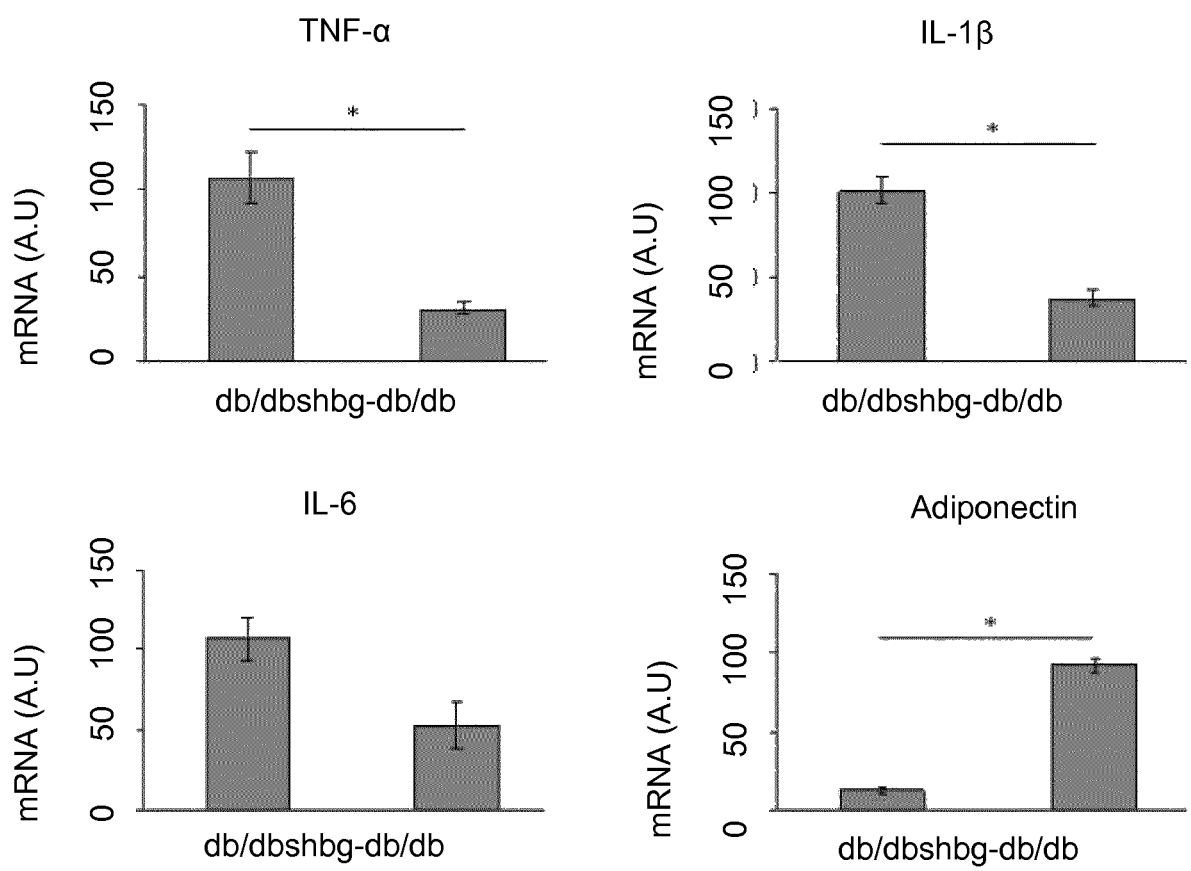
FIG. 11 shows in bars in the Y-axis the mRNA levels (mRNA) of TNF-α (panel A), of IL-1β (panel B), of IL6 (panel C), and of Adiponectin (panel D), between db/db and shbg-db/db transgenic mice (indicated in the X-axis as sample types or S).

For these two genotypes it was also determined the expression of several proinflammatory cytokines (TNF-α, IL-6 and IL-1β) and adiponectin in adipose tissue. The results, in FIG. 11, showed that mRNA levels (Arbitrary units relative to 18S mRNA levels) of tumoral necrosis factor-α (TNF-α) and interleukin 1β (IL-1β) were significantly reduced in shbg-db/db when compared with db/db mice (FIG. 11, panels A and B, respectively). The interleukin 6 (IL6) mRNA levels (depicted in FIG. 11 panel C) were reduced in shbg-db/db mice when compared with db/db mice but it was not statistically significant. Adiponectin mRNA levels (FIG. 11, panel D) were increased significantly in shbg-db/db mice when compared with db/db mice.

All the mRNA levels were determined in adipose tissue as indicated in example 3.4 for adipose tissue.

```
Primers for TNF-α (in 5'-3' direction):
Forward,
                                        (SEQ ID NO: 11)
CATCTTCTCAAAATTCGAGTGACAA;

Reverse,
                                        (SEQ ID NO: 12)
TGGGAGTAGACAAGGTACAACCC.

Primers for IL-β(in 5'-3' direction):
Forward,
                                        (SEQ ID NO: 13)
CAACCAACAAGTGATATTCTCCATG;

Reverse,
                                        (SEQ ID NO: 14)
GATCCACACTCTCCAGCTGCA.

Primers for IL-6 (in 5'-3' direction):
Forward,
                                        (SEQ ID NO: 15)
CTGCAAGAGACTTCCATCCAGTT;

Reverse,
                                        (SEQ ID NO: 16)
GAAGTAGGGAAGGCCGTGG.

Primers for 18S (in 5'-3' direction):
Forward,
                                        (SEQ ID NO: 17)
AGGGTTCGATTCCGGAGAGG;

Reverse,
                                        (SEQ ID NO: 18)
CAACTTTAATATACGCTATTGG.

Primers for Adiponectin (in 5'-3' direction):
Forward,
                                        (SEQ ID NO: 25)
AGCCGCTTATATGTATCGCTCA;

Reverse,
                                        (SEQ ID NO: 26)
TGCCGTCATAATGATTCTGTTGG
```

FIG. 11 panel A shows in bars the mRNA levels (mRNA) of TNF-α, between db/db and shbg-db/db mice; FIG. 11 panel B, shows in bars the mRNA levels (mRNA) of IL-1β, between db/db and shbg-db/db mice; FIG. 11 panel C, shows in bars the mRNA levels (mRNA) of IL6, between db/db and shbg-db/db mice; and FIG. 11 panel D, shows in bars the mRNA levels (mRNA) of Adiponectin, between db/db and shbg-db/db mice.

3.6. SHBG Production is Reduced by the Alteration of HNF-4α and PPARγ Protein Levels in Human shbg-db/db Transgenic Mice.

Figure 12:
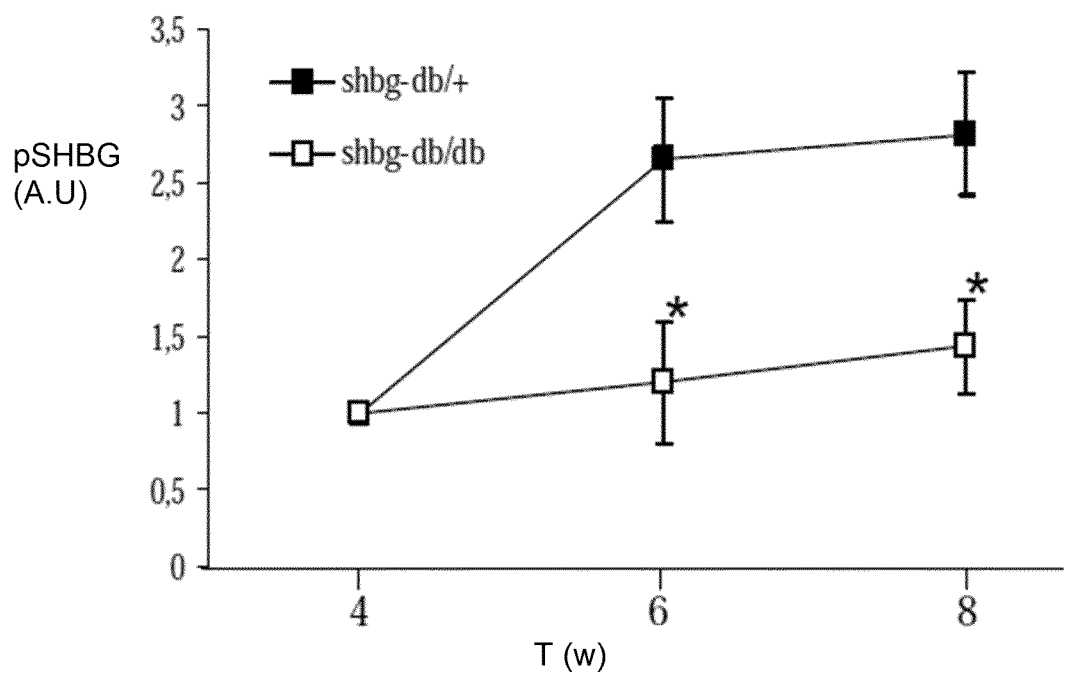
FIG. 12 is a graphic showing in the Y-axis the plasma levels (relative levels with respect to the plasma SHBG levels of each mice at 4 weeks of age) of SHBG (pSHBG) measured in lean shbg-db/+ and obese shbg-db/db mice up to 8 weeks of age. X-axis shows the time (T) in weeks (w). Data from lean shbg-db/+ mice are indicated in black-square marks. Data from obese shbg-db/db mice are indicated in white-square marks.

The inventors also studied the SHBG regulation in the shbg-db/db transgenic mice. Plasma SHBG levels were measured in lean shbg-db/+ and obese shbg-db/db mice up to 8 weeks of age. The lean shbg-db/+ mice showed an increase in plasma SHBG levels from 4 to 6 weeks of age and the levels remained constant until 8 weeks (FIG. 12, black-square marks). However, the plasma SHBG levels in obese shbg-db/db mice did not increase from week 4 to week 6 and remained lower at 8 weeks of age (FIG. 12, white-square marks.

Plasma analysis of SHBG was performed using an ELISA from DEMEDITEC Diagnostics GmbH (REF DE2996).

Figure 13:
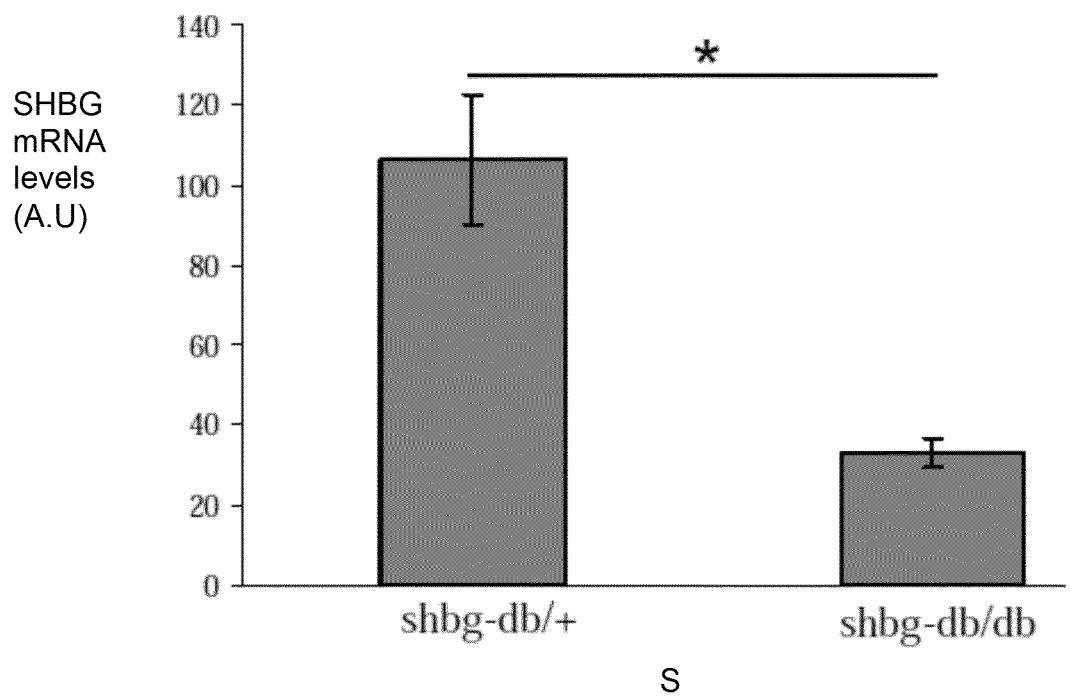
FIG. 13 shows in bars (Y-axis) the SHBG mRNA levels (Arbitrary units relative to 18S mRNA levels) in the liver of lean shbg-db/+ and obese shbg-db/db mice at 6 weeks of age. Each genotype is indicated in the X-axis (Sample, S) under the corresponding results bars.

The hepatic SHBG expression was also determined in lean shbg-db/+ and obese shbg-db/db mice at 6 weeks of age. The results showed that obese shbg-db/db mice had a significant decreased in SHBG mRNA levels when compared with lean shbg-db/+ mice (FIG. 13). FIG. 13 shows the levels of SHBG mRNA (Arbitrary units relative to 18S mRNA levels) for each tested genotype.

For the mRNA analysis, total RNA was extracted from mouse livers samples using TRIzol reagent (Invitrogen SA). Reverse transcription (RT) was performed at 42° C., for 50 min using 3 μg of total RNA and 200 U of Superscript II together with an oligo-dT primer and reagents provided by Invitrogen. An aliquot of the RT product was amplified in a 25-μl reaction using SYBR Green (Invitrogen SA) with appropriate oligonucleotide primer pairs (see below) corresponding to human SHBG. Results were analyzed using the 7000 SDS program.

```
Primers for hSHBG (in 5'-3' direction):
Forward,
                                        (SEQ ID NO: 19)
GCTGATTATGGAGAGCAGAGG;

Reverse,
                                        (SEQ ID NO: 20)
GGTCATGACAGCGATAGGCT.
```

Figure 14:
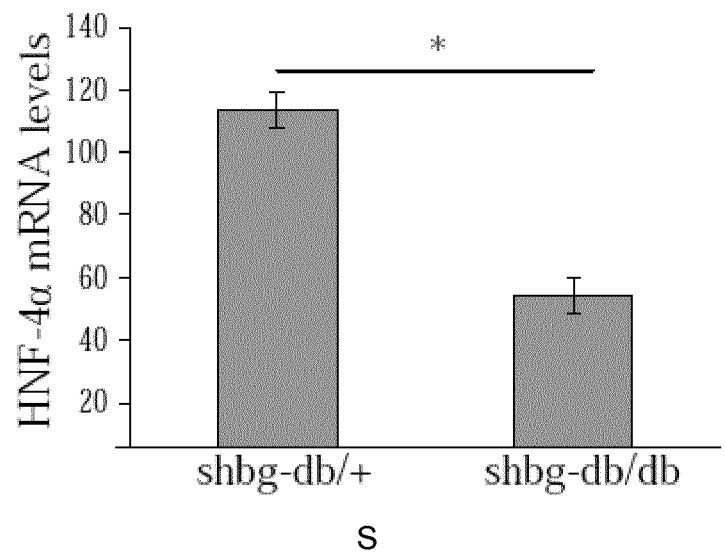
FIG. 14 is another bar diagram with the mRNA levels (Arbitrary units relative to 18S mRNA levels) of HNF-4α (panel A) and PPARγ (panel B) in the Y-axis. The genotypes tested (S) in the X-axis under the corresponding bar are the same as in FIG. 13.
Figure 14:
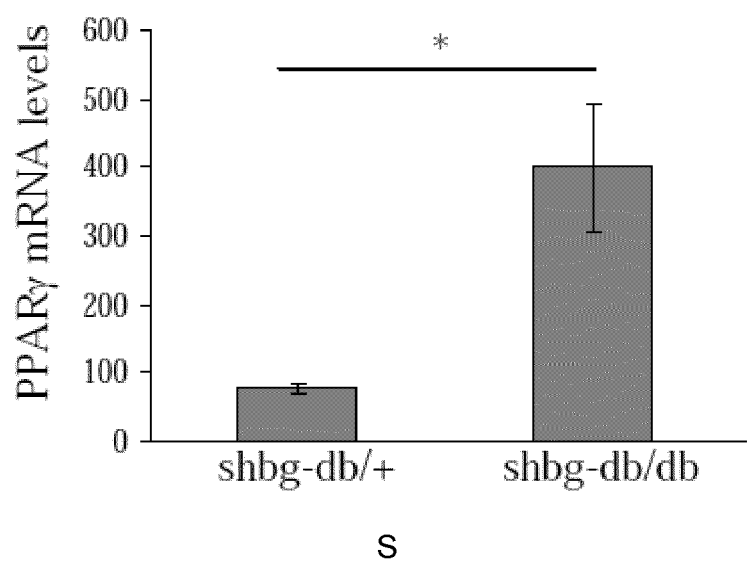
Figure 15:
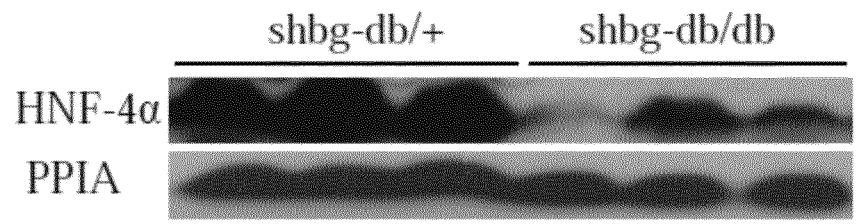
FIG. 15 is a western blot image showing the HNF-4α and PPARγ protein levels in obese shbg-db/db and lean shbg-db/+ mice. PPIA (control) is Peptidylprolylisomerase A.
Figure 15:
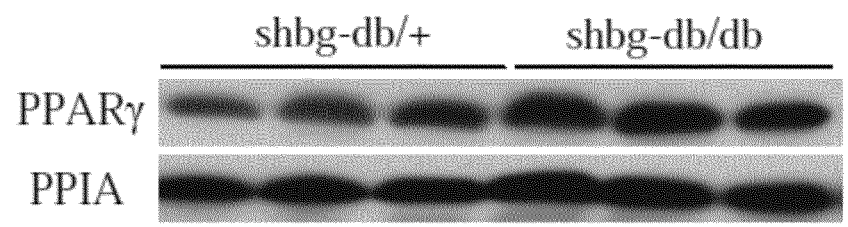

Given that HNF-4α and Peroxisome proliferator-activated receptor gamma (PPARγ) transcription factors play a role in the transcriptional activity of the human SHBG gene, it was analyzed the hepatic HNF-4α and PPARγ levels in lean shbg-db/+ and obese shbg-db/db transgenic mice. The results showed that obese shbg-db/db mice had significantly reduced HNF-4α and increased PPARγ mRNA levels when compared with lean shbg-db/+ mice. These data are derived from FIG. 14, panels A and B, respectively, wherein a bar diagram indicates (Y-axis) the mRNA levels of HNF-4α (panel A) and PPARγ (panel B). Moreover, obese shbg-db/db mice had significantly reduced HNF-4α and increased PPARγ protein levels when compared with lean shbg-db/+ mice. Protein data results are depicted in FIG. 15 (panels A and B), wherein a western blot assays shows lower protein levels of HNF-4α (panel A) in shbg-db/db mice in relation to shbg-db/+ mice. On the other side, the western blot assay for PPARγ(panel B) protein levels shows higher levels in shbg-db/db mice than in lean shbg-db/+ mice.

For the analysis of mRNA levels, and as indicated for the levels of SHBG, total RNA was extracted from mouse livers using TRIzol reagent (Invitrogen SA). Reverse transcription (RT) was performed at 42° C., for 50 min using 3 μg of total RNA and 200 U of Superscript II together with an oligo-dT primer and reagents provided by Invitrogen. An aliquot of the RT product was amplified in a 25-μl reaction using SYBR Green (Invitrogen SA) with appropriate oligonucleotide primer pairs (see below) corresponding to mouse HNF-4α and mouse PPARγ. Results were analyzed using the 7000 SDS program.

```
Primers for HNF-4α (in 5'-3' direction):
Forward,
                                (SEQ ID NO: 21)
GTGGCGAGTCCTTATGACACG;

Reverse,
                                (SEQ ID NO: 22)
CACATTGTCGGCTAAACCTGC.

Primers for PPARγ (in 5'-3' direction):
Forward,
                                (SEQ ID NO: 23)
TCTTAACTGCCGGATCCACAA;

Reverse,
                                (SEQ ID NO: 24)
GCCCAAACCTGATGGCATT.
```

In the same way as in example 3.4, the protein analysis was performed by homogenized mouse livers in RIPA RIPA (Radioimmunoprecipitation assay buffer) buffer with Complete™ protease inhibitor cocktail (Roche Diagnostics, Barcelona, Spain). Protein extracts were used for western blotting with antibodies against HNF-4α (C-19; catalog sc-6556; Santa Cruz Biotechnology Inc., Santa Cruz, Calif., USA), PPARγ (H-100; catalog sc-7196; Santa Cruz Biotechnology Inc.). Specific antibody-antigen complexes were identified using the corresponding HRP-labeled rabbit anti-goat IgG, rabbit anti-mouse IgG or goat anti-rabbit IgG and chemiluminescent substrates (Millipore) by exposure to x-ray film.

As a whole, these results showed that SHBG-db/db mice is a good model to elucidate the molecular mechanism by which SHBG exert its actions.

Finally, to demonstrate that SHBG downregulation in obese shbg-db/db mice was caused by the decrease in HNF-4α and the increased in PPARγ protein levels, chromatin immunoprecipitation (ChIP) assays were performed using DNA/protein complexes extracted from livers of lean shbg-db/+ and obese shbg-db/db transgenic mice.

For the ChIP assays, mice livers were used with a ChIP-IT kit (Active Motif Inc.) with antibodies against HNF-4α, PPARγ, rabbit IgG or goat IgG. The purified DNA was subjected to PCR amplification (35 cycles) using specific primers below, designed to amplify a 262-bp region of the human SHBG promoter.

```
Primers for human SHBG (in 5'-3' direction):
Forward,
                                (SEQ ID NO: 27)
CTAGACCTCAGGCCTGTGAATGC;

Reverse,
                                (SEQ ID NO: 28)
GGCAGGCAGCCTTGCGTGTG
```

Figure 16:
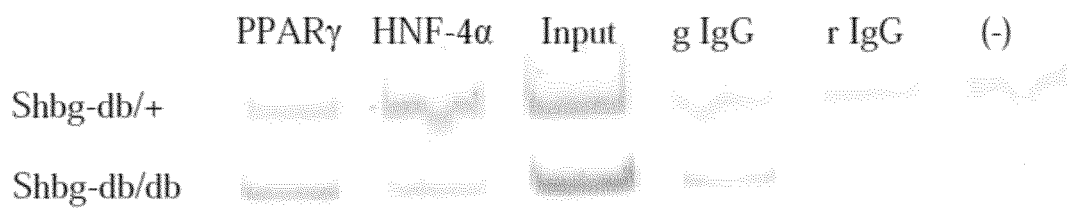
FIG. 16 is an acrylamide gel showing the PCR products of a chromatin Immunoprecipitation (ChIP) assay using specific oligonucleotides for the human SHBG promoter. As shown is the FIG. 16 antibodies against HNF-4α and PPARγ have been used. Goat and Rabbit IgGs (g IgG and r IgG) have been used as a control. Input is the initial amount of DNA used at the beginning of the assay. This

The results of chromatin immunoprecipitation are depicted in FIG. 16, wherein for each of the genotypes obese shbg-db/db mice and lean shbg-db/+ mice, it is indicated the amount of HNF-4α and PPARγ protein bound to the human SHBG promoter in the liver of shbg-db/+ and shbg-db/db mice. The bands of SHBG promoters from obese shbg-db/db mice had less HNF-4α and more PPARγ binding than the lean shbg-db/+ mice.

Example 4

SHBG mRNA Expression is Inversely Associated with Total Liver Triglyceride Content in Human Liver Biopsies, and SHBG mRNA Levels are Associated with HNF-4α and PPARγ2 mRNA Expression The SHBG gene expression levels in human liver biopsies was also analyzed from 15 individuals covering a range of Body Mass Index (BMI) between 32 and 52. The results, in FIG. 17 (A), indicated that SHBG mRNA levels were negatively correlated with BMI ($r=-0.629$, $P<0.05$). Next it was assessed if SHBG mRNA levels were also inversely associated with total triglyceride content from the 15 liver biopsies. The results, in FIG. 17 (B) showed that SHBG mRNA levels also correlates negatively with total liver triglyceride content ($r=-0.643$, $P<0.01$).

Thus, low levels of SHBG are associated with fatty liver.

This can also be deduced from the correlation of ACC mRNA levels, important enzyme that regulates hepatic lipogenesis, with SHBG mRNA levels in these 15 liver biopsies. As derivable from FIG. 17 (E), SHBG mRNA levels were negatively correlated with ACC mRNA levels ($r=0.2868$, $P<0.012$). Analysis of ACC mRNA levels was performed in the human biopsies with the primers and protocols as disclosed in example 3.4 for mouse liver biopsies.

In addition, since hepatic SHBG expression in humans is regulated by HNF-4α and PPARγ2 (See for example Selva et al., "Peroxisome-Proliferator Receptor γ Represses Sex Hormone Binding Globulin Expression", *Endocrinology*—2009, Vol. No.: 150(5), pp: 2183-9) it was analyzed whether the SHBG mRNA levels correlated with the mRNA levels of both transcription factors in the 15 human liver biopsies. The results showed in FIG. 17 (C and D), demonstrate that SHBG mRNA levels correlates positively with HNF-4α mRNA levels ($r=0.621$, $P<0.05$) and negatively with the PPARγ2 mRNA levels ($r=-0.643$, $P<0.05$).

For these assays (SHBG gene expression levels in human liver biopsies, and the mRNA levels of HNF-4α and PPARγ2) human liver samples were homogenized using TRIzol reagent (Invitrogen SA). Reverse transcription (RT) was performed at 42° C., for 50 min using 3 μg of total RNA and 200 U of Superscript II together with an oligo-dT primer and reagents provided by Invitrogen. An aliquot of the RT product was amplified in a 25-μl reaction using SYBR Green (Invitrogen SA) with appropriate oligonucleotide primer pairs (see below) corresponding to human HNF-4α, human PPARγ2, and human SHBG. Results were analyzed using the 7000 SDS program.

```
Primers for human HNF-4a (in 5'-3' direction):
Forward,
                                (SEQ ID NO: 29)
GCTCCTCCTTCTGCTGCTGC;

Reverse,
                                (SEQ ID NO: 30)
GGAAGAGCTTGAGACAGGCC.

Primers for human PPARγ2 (in 5'-3' direction):
Forward,
                                (SEQ ID NO: 31)
CTGGGAGATTCTCCTATTGACC;
```

```
Reverse,
                                     (SEQ ID NO: 32)
CACTTTGATTGCACTTTGGTACTC.

Primers for human 18S (in 5'-3' direction):
Forward,
                                     (SEQ ID NO: 33)
TAACGAACGAGACTCTGGCAT;

Reverse,
                                     (SEQ ID NO: 34)
CGGACATCTAAGGGCATCACAG.
```

Figure 17:
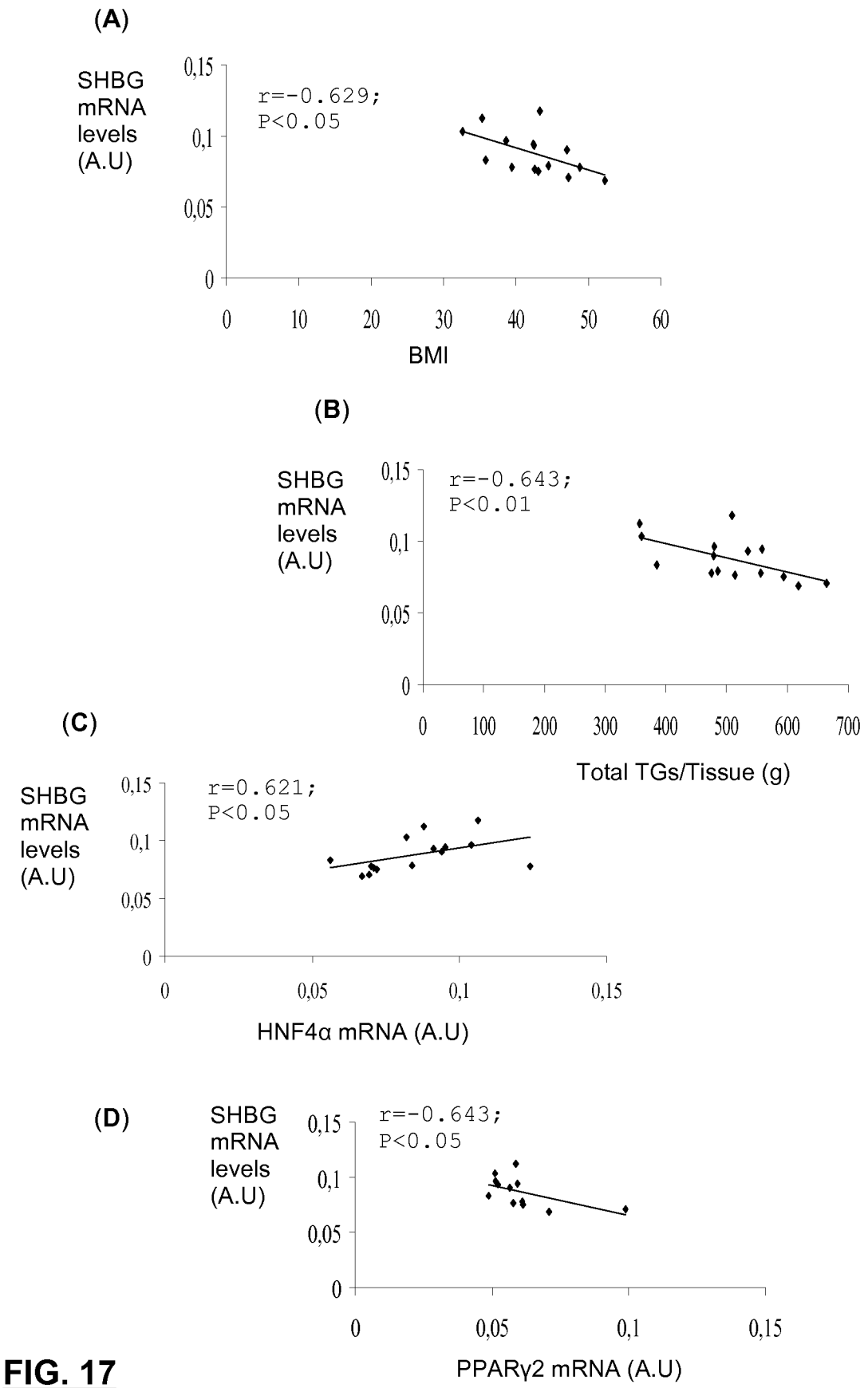
FIG. 17 shows the SHBG mRNA levels (in arbitrary units, A.U.) isolated from human liver biopsies, in relation with the body mass index (BMI) (panel A), the total triglyceride (TG) content per grams of Tissue (Total TG/Tissue g) (panel B), the HNF-4α mRNA levels (in A.U) (panel C), the PPARγ2 mRNA levels (A.U) (panel D), and the ACC mRNA levels (in A.U) (panel E).

The primers for human SHBG are the same as in Example 3.6. mRNA levels in FIG. 17 are in Arbitrary units relative to 18S mRNA levels.

Example 5

SHBG Protects Against Fatty Liver Disease Induced by High Fructose Diet

For this experiment there were used C57BL/6 mice (WT, controls) and human SHBG transgenic mice (shbg) but not obese.

SHBG transgenic mice were obtained as disclosed above and according to Jänne et al, "Human Sex-Hormone-Binding Globulin Gen Expression in Transgenic Mice", Molecular Endocrinology—1998, Vol. No. 12 (1), pp: 123-136 (supra).

Wild-type (WT) mice and shbg mice were fed with a high fructose diet. (76% fructose) for 8 weeks. Afterwards, they were sacrificed and liver biopsies were analyzed to see total triglyceride (TG) accumulation in both animal types.

Figure 18:
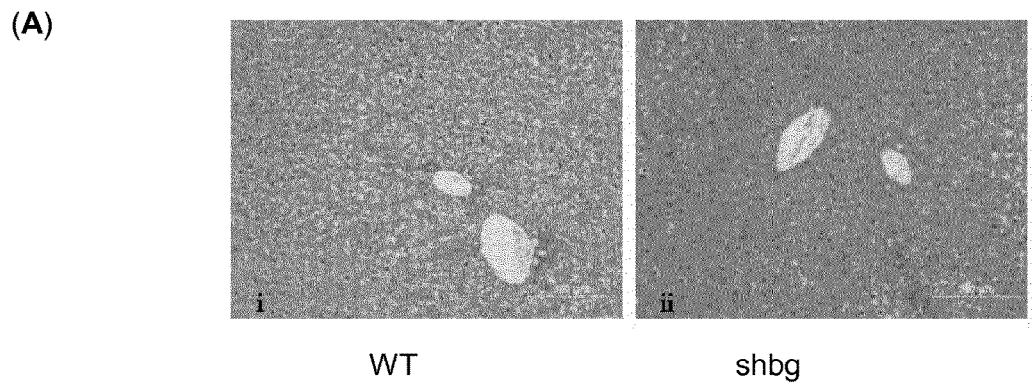
FIG. 18, relating to Example 5 depicts in Panel A the H&E histological examination of liver in wild-type mice (WT; C57BL/6 mice) and human SHBG transgenic mice (shbg). In panel B, total hepatic triglyceride (TG) content per grams of Tissue (nmol/tissue g) in wild-type and human SHBG transgenic mice. Panel C shows ACC and FAS mRNA levels (in A.U), determined in relation to 18S mRNA in wild-type (WT) and human SHBG transgenic mice (shbg). Panel D is a western blot image showing the ACC and FAS protein levels in obese human SHBG transgenic mice (shbg) and WT mice.
Figure 18:
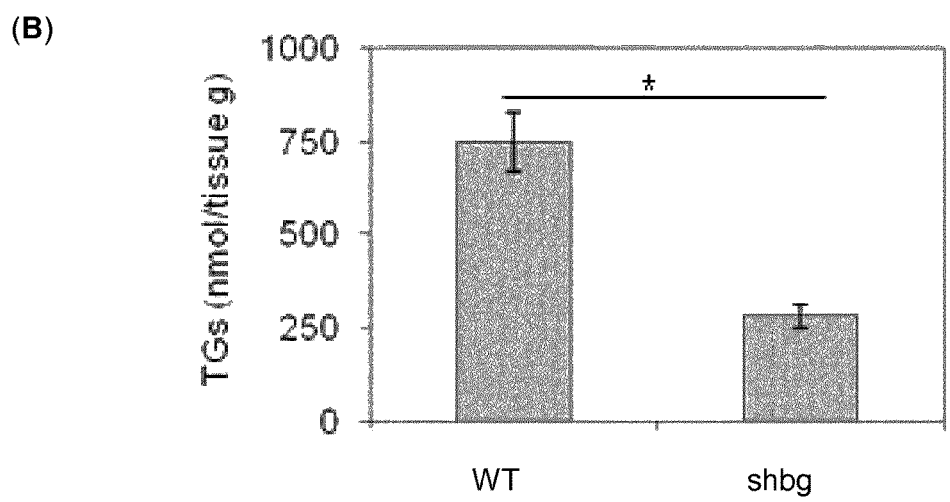
Figure 18:
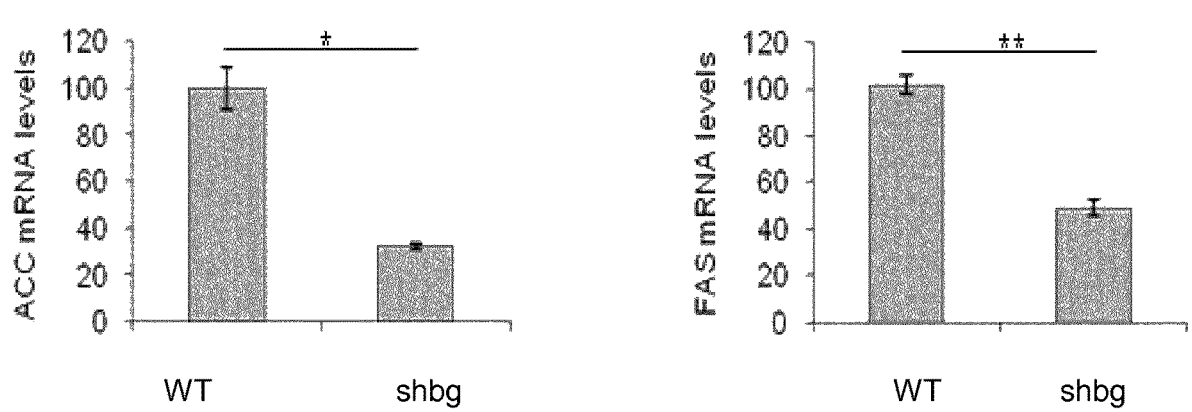

As can be seen in FIG. 18, panels (A) and (B), the triglyceride amount in liver was higher in WT mice than in the transgenic ones (shbg). In panel A, which is a shows Microscope Images (Olympus-BX61) of a paraffin section of the liver it is seen how lipid droplets in transgenic mice are smaller than WT. Panel B demonstrate the meaningful differences between both animals as TG in nmols per gram of tissue. Total triglyceride detection was measured using a triglyceride assay kit (Cat. #K622-100 BioVision) following the manufacturer's instructions.

As in Example 3.4 and following the same protocol, lipogenesis was studied by determining the mRNA and protein levels of acetyl-CoA carboxylase (ACC) and fatty acid synthase (FAS). Data from this analysis are illustrated in FIG. 18, panels (C) and (D).

From all these assays in mice fed with high fructose diet is to be concluded that SHBG acts as a prophylactic agent avoiding evolution to hepatic steatosis.

Example 6

SHBG Protects Against Obesity in Mice Fed with a High Lipid Diet

Wild-type (WT) mice and shbg-mice as in Example 5 were fed with a high lipid diet (50% lipids, from which 46% pig butter and 4% soybean fat) for 8 weeks.

Figure 19:
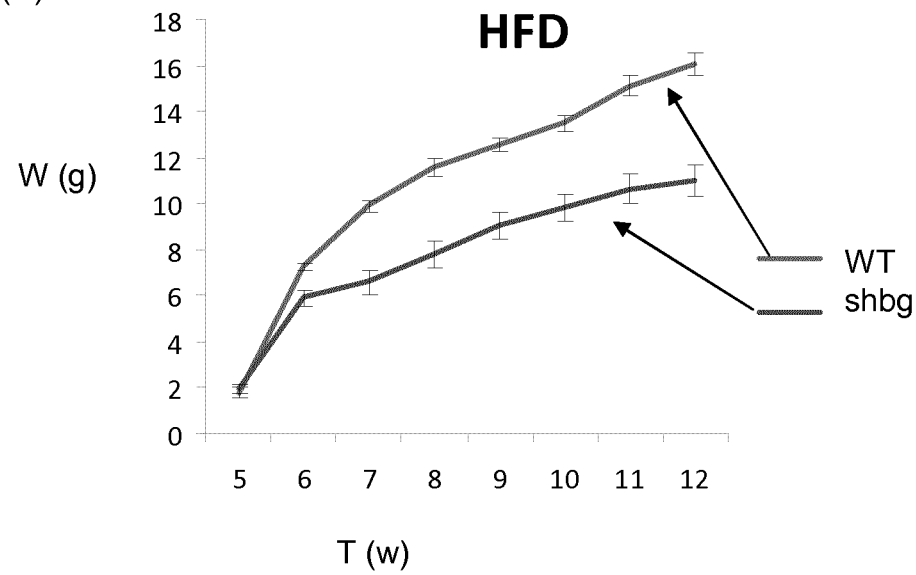
FIG. 19, relating to Example 6, shows the effect of a fat diet in wild-type mice (WT, C57BL/6 mice) and human SHBG transgenic mice (shbg).
Figure 19:
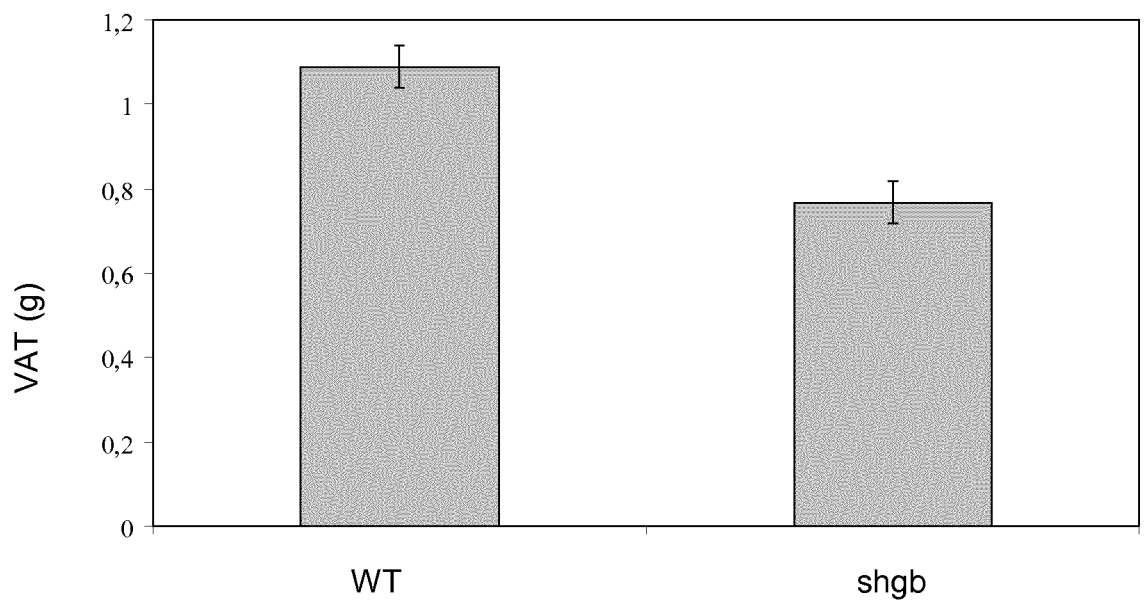

Weight increase along weeks was followed and plotted in FIG. 19 (A), wherein the weight in grams of mice is plotted per week after consumption of the fat diet. Although the weight was increasing weekly, shbg mice had always a lower weight than wild-type mice.

Once mice were sacrificed, visceral adipose tissue (VAT in grams) was analyzed in both animal types. As can be seen in FIG. 19 (B), wild-type mice had a greater visceral adipose tissue than transgenic animals, thus demonstrating that SHBG is a protector or prophylactic agent against hepatic steatosis as well as against obesity and lipid accumulation. VAT was determined as follows: all visceral fat was removed from the animals and it was weighed in a precision balance.

Example 7

Inhibition of SHBG Expression (Small-Hairpin Inhibition) Promotes Lipid (TG) Accumulation in HepG2 Cells In order to elucidate a possible mechanism of action of the SHBG, HepG2 cells (catalog no. HB-8065; ATCC) maintained in DMEM supplemented with 10% FBS and antibiotics) were stably transfected with a vector expressing SHBG (pCMV-SHBG). The vector pCMV-SHBG and the control (pCMV-empty) were the ones used and mentioned in several publications, being the first in Bocchinfuso W P et al. "Expression and differential glycosylation of human sex hormone-binding globulin by mammalian cell lines", Mol Endocrinol-1991, Vol. No. 5(11)., pp. 1723-1729.

In a parallel assay HepG2 cells were stably transfected with a commercial (Sigma Aldrich) small-hairpin RNA to quench mRNA of SHBG (pIKO.1-SHBG) or pIKO.1-scramble oligo as a control.

Figure 20:
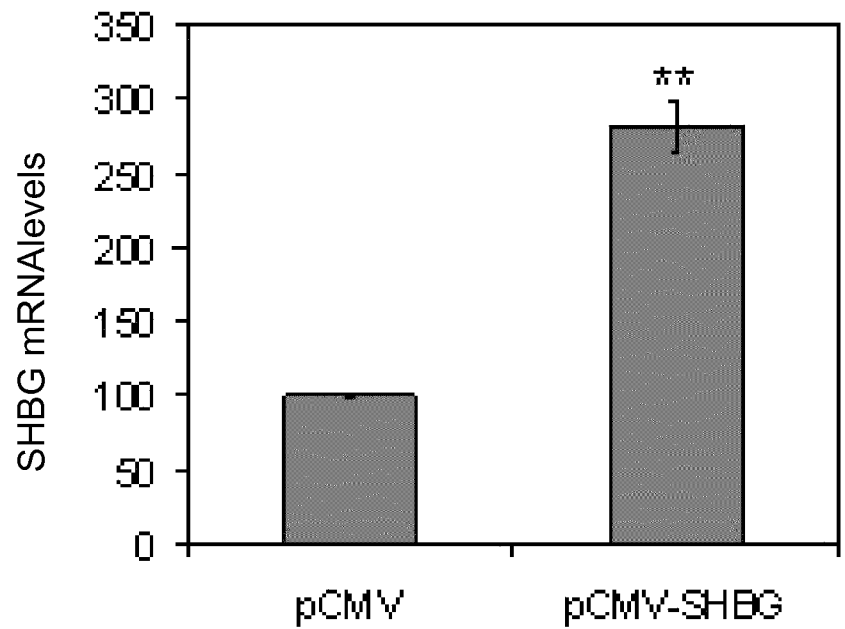
FIG. 20, relating to Example 7, shows several data retrieved from an assay in HepG2 cells, in which SHGB has been overexpressed (pCMV-SHGB), or expression has been suppressed (shSHBG). The controls of each of the assays were, respectively, the vector without the fragment encoding the SHBG (pCMV) and the shvector with scramble oligo (shControl).
Figure 20:
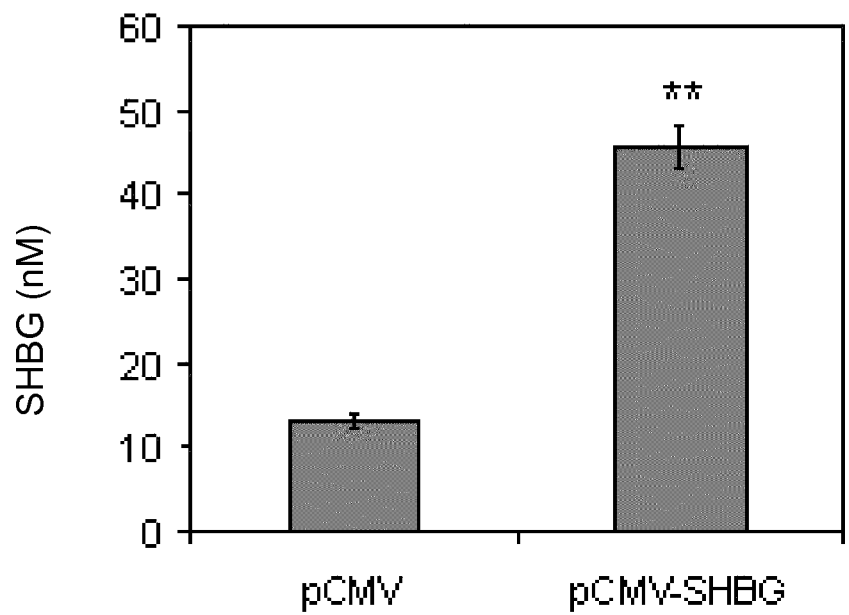

From all panels in FIG. 20 it can be deduced that SHBG regulates hepatocyte lipid content by modulating ACC levels in HepG2 cells. (a) SHBG mRNA levels were determined in relation to 18S RNA in pCMV and pCMV-SHBG stably transfected HepG2 cells (FIG. 20 a). SHBG protein accumulation in the medium was measured using an ELISA in pCMV and pCMV-SHBG stably transfected HepG2 cells (FIG. 20 b). ACC mRNA levels were determined in relation to 18S mRNA in pCMV and pCMV-SHBG stably transfected HepG2 cells (FIG. 20 c). SHBG mRNA levels were determined in relation to 18S RNA in shControl and shSHBG stably transfected HepG2 cells (FIG. 20 d). SHBG protein accumulation in the medium was measured using an ELISA in shControl and shSHBG stably transfected HepG2 cells (FIG. 20 e). ACC mRNA levels were determined in relation to 18S RNA in shControl and shSHBG stably transfected HepG2 cells (FIG. 20 f). ACC protein levels were measured by Western blotting using PPIA as a housekeeping reference protein in pCMV and pCMV-SHBG stably transfected HepG2 cells (FIG. 20 g). ACC protein levels were measured by Western blotting using PPIA as a housekeeping reference protein in shControl and shSHBG stably transfected HepG2 cells (FIG. 20 h). Total triglyceride (TG in nmols/mg of protein) content measured in pCMV and pCMV-SHBG stably transfected HepG2 cells can be seen in FIG. 20 (i). Total triglyceride content (TG in nmols/mg of protein) measured in shControl and shSHBG stably transfected HepG2 cells can be seen in FIG. 20 j. Data points are mean±SD of triplicate measurements. **P<0.01 and *P<0.05.

In both cell assays, detection of SHBG mRNA levels, and protein concentration of SHBG was performed as illustrated in Example 3.6, ACC mRNA levels were determined as disclosed in Example 3.4. For the western blot there were followed the protocols as illustrated in Example 3.4 with the ACCα and PPIA antibodies. Finally, TG were measured using a triglyceride assay kit (Cat. #K622-100 BioVision) following the manufacturer's instructions.

The data from FIG. 20 allow concluding that if SHBG is over-expressed in HepG2 cells the total TG is reduced (FIG.

20 i), contrary to HepG2 cells, in which expression of SHBG is inhibited (FIG. 20 j). In addition, this seems related with ACC expression (FIG. 20 g and h), in such a way that when SHBG is over-expressed the expression of ACC is reduced (FIG. 20 g); and when SHBG expression is inhibited, ACC expression is augmented (FIG. 20 h) in relation to controls.

All these examples allow concluding that SHBG significantly reduced body weight gain, hepatic steatosis, visceral fat accumulation and inflammation in mice. Moreover, it was determined that low SHBG levels found in obese mice were reduced by a decrease in hepatic HNF-4α and increase in PPARγ levels. Finally, using human liver biopsies it has been found that SHBG mRNA levels correlates negatively with total liver triglyceride content.

Therefore, the SHBG and/or a fragment thereof can be used in obesity, overweight and hepatic steatosis treatment.

In addition, due to its lipoliytic role, the SHBG and/or a fragment thereof can be used cosmetically to reduce fat stores located subcutaneously in order to improve the bodily appearance of a mammal, in particular a human.

REFERENCES CITED IN THE APPLICATION

EP1541127B1
Sutton-Tyrrell et al., "Sex-hormone-binding Globulin and the free androgen index are related to cardiovascular risk factors in multiethnic premenopausal and perimenopausal women enrolled in the Study of Women Across the Nation (SWAN)", *Circulation*—2005, Vol. No. 111., pp: 1242-1249.

Kalme et al., "Sex hormone-binding globulin and insulin-like growth factor-binding protein-1 as indicators of metabolic syndrome, cardiovascular risk, and mortality in elderly men", *J. Clin. Endocrinol. Metab*—2004, Vol. No. 90, pp: 1550-1556.

Stefan et al. "Sex-Hormone-Binding Globulin and Risk of Type 2 Diabetes", *The New England Journal of Medicine*—2009, 361, pp. 2675-2678.

Selva et al, "Monosaccharide-induced lipogenesis regulates the human hepatic sex hormone-binding globulin gene", *The Journal of Clinical Investigation*—2007, Vol. NO. 117 (12), pp: 3979-3987.

Selva et al., "Peroxisome-Proliferator Receptor γ Represses Sex Hormone Binding Globulin Expression", *Endocrinology*—2009, Vol. No.: 150(5), pp: 2183-9.

Bocchinfuso W P et al. "Expression and differential glycosylation of human sex hormone-binding globulin by mammalian cell lines", Mol Endocrinol—1991, Vol. No. 5(11)., pp. 1723-1729.

The invention claimed is:

1. A method of reducing lipid content in mammal hepatocytes comprising:
administering a therapeutically effective amount of an isoform of the human sex hormone-binding globulin comprising the amino acid sequence selected from the group consisting of SEQ ID NO: 1, SEQ ID NO: 2, SEQ ID NO: 3, SEQ ID NO: 4, SEQ ID NO: 5 and mixtures thereof, together with pharmaceutically acceptable excipients or carriers.

2. A method for one or both treating or preventing hepatic steatosis in a mammal, including human, the method comprising:
administering a therapeutically effective amount of an isoform of the human sex hormone binding globulin comprising the amino acid sequence selected from the group consisting of SEQ ID NO: 1, SEQ ID NO: 2, SEQ ID NO: 3, SEQ ID NO: 4, SEQ ID NO: 5 and mixtures thereof, together with one or both pharmaceutically acceptable excipients or carriers.

3. The method of claim 2, the isoform of the human sex hormone-binding globulin being an ingredient of a pharmaceutical composition for parenteral administration.

4. A method of reducing lipids in an isolated sample comprising mammal hepatocytes, the method comprising:
administering an isoform of the human sex hormone-binding globulin comprising the amino acid sequence selected from the group consisting of SEQ ID NO: 1, SEQ ID NO: 2, SEQ ID NO: 3, SEQ ID NO: 4, SEQ ID NO: 5 and mixtures thereof.

* * * * *

SEQUENCE LISTING

```
<160> NUMBER OF SEQ ID NOS: 34

<210> SEQ ID NO 1
<211> LENGTH: 402
<212> TYPE: PRT
<213> ORGANISM: Homo sapiens

<400> SEQUENCE: 1

Met Glu Ser Arg Gly Pro Leu Ala Thr Ser Arg Leu Leu Leu Leu Leu
1               5                   10                  15

Leu Leu Leu Leu Leu Arg His Thr Arg Gln Gly Trp Ala Leu Arg Pro
            20                  25                  30

Val Leu Pro Thr Gln Ser Ala His Asp Pro Pro Ala Val His Leu Ser
        35                  40                  45

Asn Gly Pro Gly Gln Glu Pro Ile Ala Val Met Thr Phe Asp Leu Thr
    50                  55                  60

Lys Ile Thr Lys Thr Ser Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
                85                  90                  95

Met Leu Gly Leu Arg Asp Gly Arg Pro Glu Ile Gln Leu His Asn His
                100                 105                 110

Trp Ala Gln Leu Thr Val Gly Ala Gly Pro Arg Leu Asp Asp Gly Arg
            115                 120                 125

Trp His Gln Val Glu Val Lys Met Glu Gly Asp Ser Val Leu Leu Glu
        130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu
                165                 170                 175

Phe Pro Ala Ser Asn Leu Arg Leu Pro Leu Val Pro Ala Leu Asp Gly
            180                 185                 190

Cys Leu Arg Arg Asp Ser Trp Leu Asp Lys Gln Ala Glu Ile Ser Ala
```

```
                195                 200                 205
Ser Ala Pro Thr Ser Leu Arg Ser Cys Asp Val Glu Ser Asn Pro Gly
210                 215                 220

Ile Phe Leu Pro Pro Gly Thr Gln Ala Glu Phe Asn Leu Arg Asp Ile
225                 230                 235                 240

Pro Gln Pro His Ala Glu Pro Trp Ala Phe Ser Leu Asp Leu Gly Leu
                245                 250                 255

Lys Gln Ala Ala Gly Ser Gly His Leu Leu Ala Leu Gly Thr Pro Glu
                260                 265                 270

Asn Pro Ser Trp Leu Ser Leu His Leu Gln Asp Gln Lys Val Val Leu
                275                 280                 285

Ser Ser Gly Ser Gly Pro Gly Leu Asp Leu Pro Leu Val Leu Gly Leu
290                 295                 300

Pro Leu Gln Leu Lys Leu Ser Met Ser Arg Val Val Leu Ser Gln Gly
305                 310                 315                 320

Ser Lys Met Lys Ala Leu Ala Leu Pro Pro Leu Gly Leu Ala Pro Leu
                325                 330                 335

Leu Asn Leu Trp Ala Lys Pro Gln Gly Arg Leu Phe Leu Gly Ala Leu
                340                 345                 350

Pro Gly Glu Asp Ser Ser Thr Ser Phe Cys Leu Asn Gly Leu Trp Ala
                355                 360                 365

Gln Gly Gln Arg Leu Asp Val Asp Gln Ala Leu Asn Arg Ser His Glu
                370                 375                 380

Ile Trp Thr His Ser Cys Pro Gln Ser Pro Gly Asn Gly Thr Asp Ala
385                 390                 395                 400

Ser His

<210> SEQ ID NO 2
<211> LENGTH: 288
<212> TYPE: PRT
<213> ORGANISM: Homo sapiens

<400> SEQUENCE: 2

Pro Arg Phe Lys Gly Ser Pro Ala Val Leu Phe Lys Leu Thr Tyr Ala
1               5                   10                  15

Val Ile Thr Cys Phe Ser Leu Arg Leu Thr His Pro Arg Pro Trp
                20                  25                  30

Ser Ala His Asp Pro Pro Ala Val His Leu Ser Asn Gly Pro Gly Gln
                35                  40                  45

Glu Pro Ile Ala Val Met Thr Phe Asp Leu Thr Lys Ile Thr Lys Thr
50                  55                  60

Ser Ser Ser Phe Glu Val Arg Thr Trp Asp Pro Glu Gly Val Ile Phe
65                  70                  75                  80

Tyr Gly Asp Thr Asn Pro Lys Asp Asp Trp Phe Met Leu Gly Leu Arg
                85                  90                  95

Asp Gly Arg Pro Glu Ile Gln Leu His Asn His Trp Ala Gln Leu Thr
                100                 105                 110

Val Gly Ala Gly Pro Arg Leu Asp Asp Gly Arg Trp His Gln Val Glu
                115                 120                 125

Val Lys Met Glu Gly Asp Ser Val Leu Leu Glu Val Asp Gly Glu Glu
                130                 135                 140

Val Leu Arg Leu Arg Gln Val Ser Gly Pro Leu Thr Ser Lys Arg His
145                 150                 155                 160

Pro Ile Met Arg Ile Ala Leu Gly Gly Leu Leu Phe Pro Ala Ser Asn
```

```
                    165                 170                 175

Leu Arg Leu Pro Leu Val Pro Ala Leu Asp Gly Cys Leu Arg Arg Asp
            180                 185                 190

Ser Trp Leu Asp Lys Gln Ala Glu Ile Ser Ala Ser Ala Pro Thr Ser
            195                 200                 205

Leu Arg Ser Cys Asp Val Glu Ser Asn Pro Gly Ile Phe Leu Pro Pro
210                 215                 220

Gly Thr Gln Ala Glu Phe Asn Leu Arg Asp Ile Pro Gln Pro His Ala
225                 230                 235                 240

Glu Pro Trp Ala Phe Ser Leu Asp Leu Gly Leu Lys Gln Ala Ala Gly
                245                 250                 255

Ser Gly His Leu Leu Ala Leu Gly Thr Pro Glu Asn Pro Ser Trp Leu
            260                 265                 270

Ser Leu His Leu Gln Asp Gln Glu Lys Thr Leu Pro Pro Leu Phe Ala
            275                 280                 285

<210> SEQ ID NO 3
<211> LENGTH: 293
<212> TYPE: PRT
<213> ORGANISM: Homo sapiens

<400> SEQUENCE: 3

Met Glu Ser Arg Gly Pro Leu Ala Thr Ser Arg Leu Leu Leu Leu Leu
1               5                   10                  15

Leu Leu Leu Leu Leu Arg His Thr Arg Gln Gly Trp Ala Leu Arg Pro
                20                  25                  30

Val Leu Pro Thr Gln Ser Ala His Asp Pro Pro Ala Val His Leu Ser
            35                  40                  45

Asn Gly Pro Gly Gln Glu Pro Ile Ala Val Met Thr Phe Asp Leu Thr
50                  55                  60

Lys Ile Thr Lys Thr Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
                85                  90                  95

Met Leu Gly Leu Arg Asp Gly Arg Pro Glu Ile Gln Leu His Asn His
                100                 105                 110

Trp Ala Gln Leu Thr Val Gly Ala Gly Pro Arg Leu Asp Asp Gly Arg
            115                 120                 125

Trp His Gln Val Glu Val Lys Met Glu Gly Asp Ser Val Leu Leu Glu
130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu
                165                 170                 175

Phe Pro Ala Ser Asn Leu Arg Leu Pro Leu Val Pro Ala Leu Asp Gly
            180                 185                 190

Cys Leu Arg Arg Asp Ser Trp Leu Asp Lys Gln Ala Glu Ile Ser Ala
            195                 200                 205

Ser Ala Pro Thr Ser Leu Arg Ser Cys Asp Val Glu Ser Asn Pro Gly
        210                 215                 220

Ile Phe Leu Pro Pro Gly Thr Gln Ala Glu Phe Asn Leu Arg Asp Ile
225                 230                 235                 240

Pro Gln Pro His Ala Glu Pro Trp Ala Phe Ser Leu Asp Leu Gly Leu
                245                 250                 255
```

```
Lys Gln Ala Ala Gly Ser Gly His Leu Ala Leu Gly Thr Pro Glu
            260                 265                 270

Asn Pro Ser Trp Leu Ser Leu His Leu Gln Asp Gln Glu Lys Thr Leu
            275                 280                 285

Pro Pro Leu Phe Ala
        290

<210> SEQ ID NO 4
<211> LENGTH: 287
<212> TYPE: PRT
<213> ORGANISM: Homo sapiens

<400> SEQUENCE: 4

Met Glu Ser Arg Gly Pro Leu Ala Thr Ser Arg Leu Leu Leu Leu
1               5                   10                  15

Leu Leu Leu Leu Arg His Thr Arg Gln Gly Trp Ala Leu Arg Pro
            20                  25                  30

Val Leu Pro Thr Gln Ser Ala His Asp Pro Ala Val His Leu Ser
            35                  40                  45

Asn Gly Pro Gly Gln Glu Pro Ile Ala Val Met Thr Phe Asp Leu Thr
50                  55                  60

Lys Ile Thr Lys Thr Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
            85                  90                  95

Met Leu Gly Leu Arg Asp Gly Arg Pro Glu Ile Gln Leu His Asn His
            100                 105                 110

Trp Ala Gln Leu Thr Val Gly Ala Gly Pro Arg Leu Asp Asp Gly Arg
            115                 120                 125

Trp His Gln Val Glu Val Lys Met Glu Gly Asp Ser Val Leu Leu Glu
            130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu
            165                 170                 175

Phe Pro Ala Ser Asn Leu Arg Leu Pro Leu Val Pro Ala Leu Asp Gly
            180                 185                 190

Cys Leu Arg Arg Asp Ser Trp Leu Asp Lys Gln Ala Glu Ile Ser Ala
            195                 200                 205

Ser Ala Pro Thr Ser Leu Arg Ser Cys Asp Val Glu Ser Asn Pro Gly
            210                 215                 220

Ile Phe Leu Pro Pro Gly Thr Gln Ala Glu Phe Asn Leu Arg Gly Glu
225                 230                 235                 240

Asp Ser Ser Thr Ser Phe Cys Leu Asn Gly Leu Trp Ala Gln Gly Gln
            245                 250                 255

Arg Leu Asp Val Asp Gln Ala Leu Asn Arg Ser His Glu Ile Trp Thr
            260                 265                 270

His Ser Cys Pro Gln Ser Pro Gly Asn Gly Thr Asp Ala Ser His
            275                 280                 285

<210> SEQ ID NO 5
<211> LENGTH: 384
<212> TYPE: PRT
<213> ORGANISM: Homo sapiens

<400> SEQUENCE: 5
```

Met Glu Ser Arg Gly Pro Leu Ala Thr Ser Arg Leu Leu Leu Leu
1               5                   10                  15

Leu Leu Leu Leu Leu Arg His Thr Arg Gln Gly Trp Ala Leu Arg Pro
                20                  25                  30

Val Leu Pro Thr Gln Ser Ala His Asp Pro Pro Ala Val His Leu Ser
            35                  40                  45

Asn Gly Pro Gly Gln Glu Pro Ile Ala Val Met Thr Phe Asp Leu Thr
50                  55                  60

Lys Ile Thr Lys Thr Ser Ser Phe Glu Val Arg Thr Trp Asp Pro
65                  70                  75                  80

Glu Gly Val Ile Phe Tyr Gly Asp Thr Asn Pro Lys Asp Asp Trp Phe
                85                  90                  95

Met Leu Gly Leu Arg Asp Gly Arg Pro Glu Ile Gln Leu His Asn His
            100                 105                 110

Trp Ala Gln Leu Thr Val Gly Ala Gly Pro Arg Leu Asp Asp Gly Arg
            115                 120                 125

Trp His Gln Val Glu Val Lys Met Glu Gly Asp Ser Val Leu Leu Glu
        130                 135                 140

Val Asp Gly Glu Glu Val Leu Arg Leu Arg Gln Val Ser Gly Pro Leu
145                 150                 155                 160

Thr Ser Lys Arg His Pro Ile Met Arg Ile Ala Leu Gly Gly Leu Leu
                165                 170                 175

Phe Pro Ala Ser Asn Leu Arg Leu Pro Ala Glu Ile Ser Ala Ser Ala
            180                 185                 190

Pro Thr Ser Leu Arg Ser Cys Asp Val Glu Ser Asn Pro Gly Ile Phe
            195                 200                 205

Leu Pro Pro Gly Thr Gln Ala Glu Phe Asn Leu Arg Asp Ile Pro Gln
210                 215                 220

Pro His Ala Glu Pro Trp Ala Phe Ser Leu Asp Leu Gly Leu Lys Gln
225                 230                 235                 240

Ala Ala Gly Ser Gly His Leu Leu Ala Leu Gly Thr Pro Glu Asn Pro
                245                 250                 255

Ser Trp Leu Ser Leu His Leu Gln Asp Gln Lys Val Val Leu Ser Ser
            260                 265                 270

Gly Ser Gly Pro Gly Leu Asp Leu Pro Leu Val Leu Gly Leu Pro Leu
            275                 280                 285

Gln Leu Lys Leu Ser Met Ser Arg Val Val Leu Ser Gln Gly Ser Lys
        290                 295                 300

Met Lys Ala Leu Ala Leu Pro Pro Leu Gly Leu Ala Pro Leu Leu Asn
305                 310                 315                 320

Leu Trp Ala Lys Pro Gln Gly Arg Leu Phe Leu Gly Ala Leu Pro Gly
                325                 330                 335

Glu Asp Ser Ser Thr Ser Phe Cys Leu Asn Gly Leu Trp Ala Gln Gly
            340                 345                 350

Gln Arg Leu Asp Val Asp Gln Ala Leu Asn Arg Ser His Glu Ile Trp
            355                 360                 365

Thr His Ser Cys Pro Gln Ser Pro Gly Asn Gly Thr Asp Ala Ser His
370                 375                 380

<210> SEQ ID NO 6
<211> LENGTH: 403
<212> TYPE: PRT
<213> ORGANISM: Mus musculus

<400> SEQUENCE: 6

```
Met Glu Lys Arg Asp Ser Val Ala Leu His Trp Arg Leu Leu Leu Leu
1               5                   10                  15

Leu Leu Leu Leu Met Pro Pro Thr His Gln Gly Arg Ala Leu Arg
            20              25                  30

His Ile Asp Pro Ile Gln Ser Ala Gln Asp Pro Pro Ala Lys Tyr Leu
            35                  40                  45

Ser Asn Gly Pro Gly Gln Glu Pro Val Met Val Met Thr Ile Asp Leu
    50                  55                  60

Thr Lys Ile Ser Lys Pro His Ser Ser Phe Glu Phe Arg Thr Trp Asp
65                  70                  75                  80

Pro Glu Gly Val Ile Phe Tyr Gly Asp Thr Asn Thr Glu Asp Asp Trp
                85                  90                  95

Phe Leu Leu Gly Leu Arg Ala Gly Gln Leu Glu Ile Gln Leu His Asn
                100                 105                 110

Ala Trp Ala Arg Leu Thr Val Gly Phe Gly Pro Arg Leu Asp Asp Gly
            115                 120                 125

Arg Trp His Pro Val Glu Leu Lys Met Asn Gly Asp Ser Leu Leu Leu
            130                 135                 140

Trp Val Asp Gly Lys Glu Met Leu Cys Leu Arg Gln Ile Ser Ala Ser
145                 150                 155                 160

Leu Ala Asp His Ser Gln Arg Ser Met Arg Ile Ala Leu Gly Gly Leu
                165                 170                 175

Leu Leu Pro Thr Ser Lys Leu Arg Phe Pro Leu Val Pro Ala Leu Asp
            180                 185                 190

Gly Cys Ile Arg Arg Asp Ile Trp Leu Gly His Gln Ala Gln Leu Ser
            195                 200                 205

Ala Ser Pro Arg Thr Ser Leu Gly Asn Cys Asp Val Asp Leu Gln Pro
210                 215                 220

Gly Leu Phe Phe Pro Pro Gly Thr His Ala Glu Phe Ser Leu Gln Asp
225                 230                 235                 240

Ile Pro Gln Pro His Ala Asp Pro Trp Thr Phe Ser Leu Glu Leu Gly
                245                 250                 255

Phe Lys Leu Val Asp Gly Ser Gly Gln Leu Leu Ala Leu Gly Thr Gly
                260                 265                 270

Thr Asn Ser Ser Trp Leu Asn Ile His Leu Gln Asn Gln Ser Val Val
            275                 280                 285

Leu Ser Ser Glu Ala Glu Pro Lys Val Val Leu Pro Leu Asp Val Gly
    290                 295                 300

Leu Pro Leu Gln Leu Thr Leu Asp Arg Val Lys Val Val Leu Ser Gln
305                 310                 315                 320

Gly Pro Lys Met Glu Val Leu Ser Met Ser Leu Leu Arg Pro Ala Ser
                325                 330                 335

Leu Trp Arg Leu Trp Ser His Pro Gln Gly His Leu Ser Leu Gly Ala
            340                 345                 350

Leu Pro Gly Glu Ser Ser Ser Ala Ser Phe Cys Leu Ser Asp Phe Trp
            355                 360                 365

Val Gln Gly Gln Arg Leu Asp Ile Asp Gln Ala Leu Ser Arg Ser Gln
    370                 375                 380

Asp Ile Trp Thr His Ser Cys Pro Gln Arg Pro Ser Asn Asp Thr Arg
385                 390                 395                 400

Thr Ser His
```

<210> SEQ ID NO 7
<211> LENGTH: 21
<212> TYPE: DNA
<213> ORGANISM: Artificial
<220> FEATURE:
<223> OTHER INFORMATION: Forward primer

<400> SEQUENCE: 7
gccattggta ttggggctta c                                    21

<210> SEQ ID NO 8
<211> LENGTH: 20
<212> TYPE: DNA
<213> ORGANISM: Artificial
<220> FEATURE:
<223> OTHER INFORMATION: Reverse primer

<400> SEQUENCE: 8
cccgaccaag gactttgttg                                      20

<210> SEQ ID NO 9
<211> LENGTH: 20
<212> TYPE: DNA
<213> ORGANISM: Artificial
<220> FEATURE:
<223> OTHER INFORMATION: Forward primer

<400> SEQUENCE: 9
ggcatcattg ggcactcctt                                      20

<210> SEQ ID NO 10
<211> LENGTH: 20
<212> TYPE: DNA
<213> ORGANISM: Artificial
<220> FEATURE:
<223> OTHER INFORMATION: Reverse primer

<400> SEQUENCE: 10
gctgcaagca cagcctctct                                      20

<210> SEQ ID NO 11
<211> LENGTH: 25
<212> TYPE: DNA
<213> ORGANISM: Artificial
<220> FEATURE:
<223> OTHER INFORMATION: Forward primer

<400> SEQUENCE: 11
catcttctca aaattcgagt gacaa                                25

<210> SEQ ID NO 12
<211> LENGTH: 23
<212> TYPE: DNA
<213> ORGANISM: Artificial
<220> FEATURE:
<223> OTHER INFORMATION: Reverse primer

<400> SEQUENCE: 12
tgggagtaga caaggtacaa ccc                                  23

<210> SEQ ID NO 13
<211> LENGTH: 25
<212> TYPE: DNA
<213> ORGANISM: Artificial
<220> FEATURE:
<223> OTHER INFORMATION: Forward primer

<400> SEQUENCE: 13
caaccaacaa gtgatattct ccatg                                          25

<210> SEQ ID NO 14
<211> LENGTH: 21
<212> TYPE: DNA
<213> ORGANISM: Artificial
<220> FEATURE:
<223> OTHER INFORMATION: Reverse primer

<400> SEQUENCE: 14
gatccacact ctccagctgc a                                              21

<210> SEQ ID NO 15
<211> LENGTH: 23
<212> TYPE: DNA
<213> ORGANISM: Artificial
<220> FEATURE:
<223> OTHER INFORMATION: Forward primer

<400> SEQUENCE: 15
ctgcaagaga cttccatcca gtt                                            23

<210> SEQ ID NO 16
<211> LENGTH: 19
<212> TYPE: DNA
<213> ORGANISM: Artificial
<220> FEATURE:
<223> OTHER INFORMATION: Reverse primer

<400> SEQUENCE: 16
gaagtaggga aggccgtgg                                                 19

<210> SEQ ID NO 17
<211> LENGTH: 20
<212> TYPE: DNA
<213> ORGANISM: Artificial
<220> FEATURE:
<223> OTHER INFORMATION: Forward primer

<400> SEQUENCE: 17
agggttcgat tccggagagg                                                20

<210> SEQ ID NO 18
<211> LENGTH: 22
<212> TYPE: DNA
<213> ORGANISM: Artificial
<220> FEATURE:
<223> OTHER INFORMATION: Reverse primer

<400> SEQUENCE: 18
caactttaat atacgctatt gg                                             22

<210> SEQ ID NO 19
<211> LENGTH: 21
<212> TYPE: DNA
<213> ORGANISM: Artificial
<220> FEATURE:
<223> OTHER INFORMATION: Forward primer

<400> SEQUENCE: 19
gctgattatg gagagcagag g                                              21

<210> SEQ ID NO 20
<211> LENGTH: 20

```
<212> TYPE: DNA
<213> ORGANISM: Artificial
<220> FEATURE:
<223> OTHER INFORMATION: Reverse primer

<400> SEQUENCE: 20
ggtcatgaca gcgataggct                                                    20

<210> SEQ ID NO 21
<211> LENGTH: 21
<212> TYPE: DNA
<213> ORGANISM: Artificial
<220> FEATURE:
<223> OTHER INFORMATION: Forward primer

<400> SEQUENCE: 21
gtggcgagtc cttatgacac g                                                  21

<210> SEQ ID NO 22
<211> LENGTH: 21
<212> TYPE: DNA
<213> ORGANISM: Artificial
<220> FEATURE:
<223> OTHER INFORMATION: Reverse primer

<400> SEQUENCE: 22
cacattgtcg gctaaacctg c                                                  21

<210> SEQ ID NO 23
<211> LENGTH: 21
<212> TYPE: DNA
<213> ORGANISM: Artificial
<220> FEATURE:
<223> OTHER INFORMATION: Forward primer

<400> SEQUENCE: 23
tcttaactgc cggatccaca a                                                  21

<210> SEQ ID NO 24
<211> LENGTH: 19
<212> TYPE: DNA
<213> ORGANISM: Artificial
<220> FEATURE:
<223> OTHER INFORMATION: Reverse primer

<400> SEQUENCE: 24
gcccaaacct gatggcatt                                                     19

<210> SEQ ID NO 25
<211> LENGTH: 22
<212> TYPE: DNA
<213> ORGANISM: Artificial
<220> FEATURE:
<223> OTHER INFORMATION: Forward primer

<400> SEQUENCE: 25
agccgcttat atgtatcgct ca                                                 22

<210> SEQ ID NO 26
<211> LENGTH: 23
<212> TYPE: DNA
<213> ORGANISM: Artificial
<220> FEATURE:
<223> OTHER INFORMATION: Reverse primer

<400> SEQUENCE: 26
```
tgccgtcata atgattctgt tgg                                        23

<210> SEQ ID NO 27
<211> LENGTH: 23
<212> TYPE: DNA
<213> ORGANISM: Artificial
<220> FEATURE:
<223> OTHER INFORMATION: Forward primer

<400> SEQUENCE: 27
ctagacctca ggcctgtgaa tgc                                        23

<210> SEQ ID NO 28
<211> LENGTH: 20
<212> TYPE: DNA
<213> ORGANISM: Artificial
<220> FEATURE:
<223> OTHER INFORMATION: Reverse primer

<400> SEQUENCE: 28
ggcaggcagc cttgcgtgtg                                            20

<210> SEQ ID NO 29
<211> LENGTH: 20
<212> TYPE: DNA
<213> ORGANISM: Artificial
<220> FEATURE:
<223> OTHER INFORMATION: Forward primer

<400> SEQUENCE: 29
gctcctcctt ctgctgctgc                                            20

<210> SEQ ID NO 30
<211> LENGTH: 20
<212> TYPE: DNA
<213> ORGANISM: Artificial
<220> FEATURE:
<223> OTHER INFORMATION: Reverse primer

<400> SEQUENCE: 30
ggaagagctt gagacaggcc                                            20

<210> SEQ ID NO 31
<211> LENGTH: 22
<212> TYPE: DNA
<213> ORGANISM: Artificial
<220> FEATURE:
<223> OTHER INFORMATION: Forward primer

<400> SEQUENCE: 31
ctgggagatt ctcctattga cc                                         22

<210> SEQ ID NO 32
<211> LENGTH: 24
<212> TYPE: DNA
<213> ORGANISM: Artificial
<220> FEATURE:
<223> OTHER INFORMATION: Reverse primer

<400> SEQUENCE: 32
cactttgatt gcactttggt actc                                       24

<210> SEQ ID NO 33
<211> LENGTH: 21
<212> TYPE: DNA
<213> ORGANISM: Artificial

```
<220> FEATURE:
<223> OTHER INFORMATION: Forward primer

<400> SEQUENCE: 33
taacgaacga gactctggca t                                      21

<210> SEQ ID NO 34
<211> LENGTH: 22
<212> TYPE: DNA
<213> ORGANISM: Artificial
<220> FEATURE:
<223> OTHER INFORMATION: Reverse primer

<400> SEQUENCE: 34
cggacatcta agggcatcac ag                                     22
```